(12) United States Patent
Zhang

(10) Patent No.: US 12,293,830 B2
(45) Date of Patent: May 6, 2025

(54) IMAGE-BASED DETECTION OF OPHTHALMIC AND SYSTEMIC DISEASES

(71) Applicant: ANTINOUS TECHNOLOGY COMPANY LIMITED, Macao (MO)

(72) Inventor: Kang Zhang, Del Mar, CA (US)

(73) Assignee: ANTINOUS TECHNOLOGY COMPANY LIMITED, Macau (MO)

( * ) Notice: Subject to any disclaimer, the term of this patent is extended or adjusted under 35 U.S.C. 154(b) by 782 days.

(21) Appl. No.: 17/488,428

(22) Filed: Sep. 29, 2021

(65) Prior Publication Data
US 2022/0165418 A1 May 26, 2022

Related U.S. Application Data

(63) Continuation of application No. PCT/CN2020/081663, filed on Mar. 27, 2020, which
(Continued)

(51) Int. Cl.
*G16H 50/20* (2018.01)
*A61B 3/12* (2006.01)
(Continued)

(52) U.S. Cl.
CPC ........... *G16H 50/20* (2018.01); *G06T 7/0012* (2013.01); *G06V 10/7747* (2022.01);
(Continued)

(58) Field of Classification Search
CPC ......... G06T 7/0012; G06T 2207/30041; G06T 2207/10101; G06T 2207/20081;
(Continued)

(56) References Cited

U.S. PATENT DOCUMENTS 5,943,116 A * 8/1999 Zeimer .................. A61B 3/145
351/221
7,220,000 B2 * 5/2007 Alster ...................... A61B 3/02
351/239

(Continued)

FOREIGN PATENT DOCUMENTS

CN 108154505 6/2018
CN 109003252 12/2018
(Continued)

OTHER PUBLICATIONS

Rehak J, Rehak M. Branch retinal vein occlusion: pathogenesis, visual prognosis, and treatment modalities. Curr Eye Res. Feb. 2008;33(2):111-31. doi: 10.1080/02713680701851902. PMID: 18293182; PMCID: PMC2430176 (Year: 2008).*

(Continued)

*Primary Examiner* — Wesley J Tucker
*Assistant Examiner* — Courtney Joan Nelson
(74) *Attorney, Agent, or Firm* — DLA PIPER LLP (US)

(57) ABSTRACT

Disclosed herein are systems, methods, devices, and media for carrying out detection of ophthalmic and systemic diseases and disorders. Deep learning algorithms enable the automated analysis of ophthalmic images such as retinal scans to generate accurate detection of various diseases and disorders. Point-of-care implementations allow for rapid and efficient detection outside of the clinical setting.

18 Claims, 20 Drawing Sheets

Related U.S. Application Data is a continuation-in-part of application No. PCT/CN2019/080525, filed on Mar. 29, 2019.

(51) Int. Cl.
| | |
|---|---|
| *G06T 7/00* | (2017.01) |
| *G06V 10/774* | (2022.01) |
| *G16H 15/00* | (2018.01) |

(52) U.S. Cl.
CPC ............ *G16H 15/00* (2018.01); *A61B 3/12* (2013.01); *G06T 2207/20081* (2013.01); *G06T 2207/20084* (2013.01); *G06T 2207/30041* (2013.01)

(58) Field of Classification Search
CPC ......... G06T 2207/20084; G06T 7/0014; G06T 2200/28; G06T 7/33; G16H 30/40; G16H 50/20; G16H 50/30; G16H 15/00; A61B 3/12; A61B 3/102; A61B 3/0025; A61B 3/14; A61B 5/4842; A61B 5/0013; A61B 3/00; A61B 5/7275; A61B 5/00; A61B 5/0033; G06V 10/82; G06V 40/193; G06V 40/18; G06V 40/197; G06V 10/771; G06V 10/7747; G06N 3/08; G06N 3/045

See application file for complete search history.

(56) References Cited

U.S. PATENT DOCUMENTS

| | | | | |
|---|---|---|---|---|
| 8,879,813 | B1 * | 11/2014 | Solanki | G06T 3/14 |
| | | | | 382/128 |
| 2007/0287932 | A1 * | 12/2007 | Huang | A61B 3/102 |
| | | | | 600/558 |

FOREIGN PATENT DOCUMENTS

| | | | | |
|---|---|---|---|---|
| DE | 112010002000 T5 * | 9/2012 | ........... | A61B 3/1233 |
| WO | WO-2017011532 A1 * | 1/2017 | | |
| WO | WO 2018/200840 | 11/2018 | | |
| WO | WO 2018/201632 | 11/2018 | | |
| WO | WO 2018/201647 | 11/2018 | | |
| WO | WO-2018222136 A1 * | 12/2018 | | |
| WO | WO 2019/218835 | 11/2019 | | |
| WO | WO-2020009292 A1 * | 1/2020 | ............... | A61B 3/10 |

OTHER PUBLICATIONS

Machine translation of WO 2020/009292 (Year: 2020).*
Ronneberger, O., Fischer, P., Brox, T. (2015). U-Net: Convolutional Networks for Biomedical Image Segmentation. In: Navab, N., Hornegger, J., Wells, W., Frangi, A. (eds) Medical Image Computing and Computer-Assisted Intervention—MICCAI 2015. MICCAI 2015. Lecture Notes in Computer Science(), vol. 935 (Year: 2015) Springer, Cham. https://doi.org/10.1007/978-3-319-24574-4_28 (Year: 2015).*
Machine translation from google patents of DE-112010002000-T5 (Year: 2012).*
Machine translation from google patents of WO-2018222136-A1 (Year: 2018).*

* cited by examiner

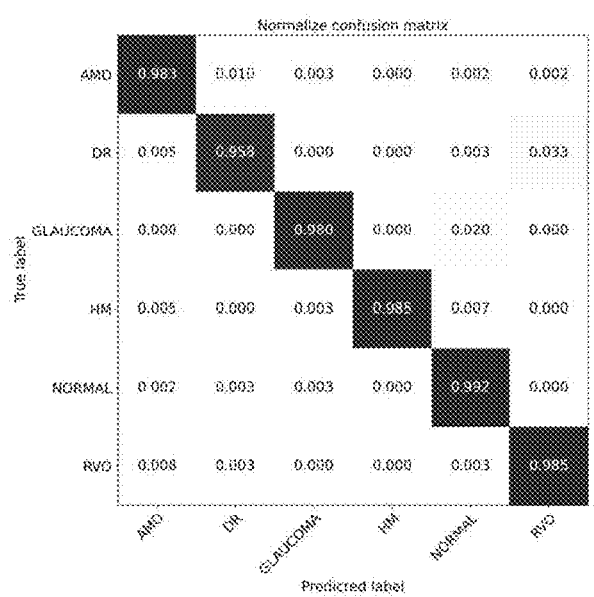
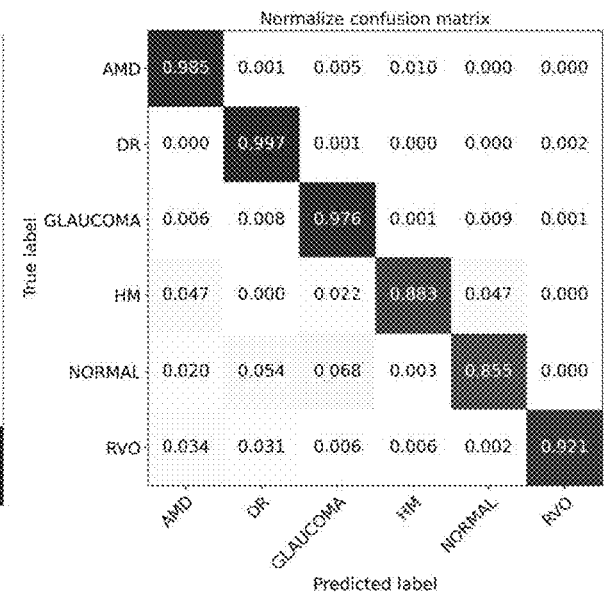
FIG. 1A                    FIG. 1B

IMAGE-BASED DETECTION OF OPHTHALMIC AND SYSTEMIC DISEASES

CROSS-REFERENCE TO RELATED APPLICATIONS

The present application is a continuation of International Patent App. No. PCT/CN2020/081663 filed Mar. 27, 2020, which claims priority to International Patent App. No. PCT/CN2019/080525 filed on Mar. 29, 2019, both of which are incorporated herein by reference herein as if set forth in full.

BACKGROUND OF THE DISCLOSURE

Despite advances in medical and surgical interventions, the burden of visual impairment remains globally high. Out of a worldwide population of 7.3 billion, an estimated 441.11 million individuals experienced some form of visual impairment in 2015, with more than 70% of cases attributed to a handful of eye conditions and 82% of cases classified as potentially avoidable. Retinal diseases, and the manifestations they carry, not only impact sight but impose serious personal and financial burdens to the patient. Visual impairment has been linked with reduced economic productivity, reduced quality of life, and increased mortality.

SUMMARY OF THE DISCLOSURE

Accordingly, systems, methods, and non-transitory computer-readable media are disclosed for automated image-based detection of ophthalmic and systemic diseases.

In an embodiment, a method is disclosed that comprises using at least one hardware processor to: receive ophthalmic image data; apply a machine-learning classifier, trained using a domain dataset of ophthalmic images that have been labeled with one or more of a plurality of classifications, to classify the received ophthalmic image data into at least one of the plurality of classifications, wherein the plurality of classifications comprise a normal classification and one or more disorder classifications, wherein the one or more disorder classifications comprise at least one of age-related macular degeneration (AMD), diabetic retinopathy (DR), glaucoma, or retinal vein occlusion (RVO); and provide a report that indicates the at least one classification of the received ophthalmic image data.

Within the dataset, the normal classification may be defined as optic discs presenting with sharp margins and a cup-to-disc ratio within a predetermined range, striated sheen from a healthy retinal nerve fiber layer, no lesions, no apparent sub-retinal disruptions, no pigmentary changes, no tumors, no scars, no molds, and normal vasculature, with an exception for drusens indicative of normal age progression. Within the dataset, the normal classification may be defined as no clinically abnormal features, no known ocular disease, and hemoglobin A1C levels less than 6.0%, with an exception for less than five drusens indicative of normal age progression. Within the dataset, AMD may be defined as advanced and late stage AMD with apparent macular damage from either dry AMD or wet AMD. Within the dataset, DR may be defined as moderate to proliferative DR, as classified according to the International Clinical Diabetic Retinopathy Disease Severity Scale. Within the dataset, diabetic macular edema (DME) may be defined as one or more of retinal thickening within 500 micrometers of a macular center, hard exudates within 500 micrometers of the macular center with adjacent retinal thickening, or one or more disc diameters of retinal thickening that are within one disc diameter of the macular center. Within the dataset, glaucoma may be defined as having one or both of concentric expansion with an optic cup-to-disc ratio greater than or equal to 0.5, or narrowing of a disc at either a superior or inferior rim with a localized nerve fiber layer defect. Within the dataset, glaucoma may be defined as having two or more of a vertical optic cup-to-disc ratio greater than or equal to 0.8, superior or inferior disc notch or rim thinning, or a retinal nerve fiber layer (RNFL) defect radiating from an optic nerve head. Within the dataset, RVO may be defined as non-ischemic and ischemic central RVO and major and macular branch RVO.

The machine-learning classifier may comprise a convolutional neural network. The method may further comprise using the at least one hardware processor to train the machine-learning classifier by: initially training the convolutional neural network to discriminate between objects using a non-domain dataset that contains no ophthalmic images labeled with the one or more disorders; subsequently retraining one or more final layers in the convolutional neural network using the domain dataset. A number of images in the non-domain dataset may be at least six times greater than a number of images in the domain dataset. The ophthalmic image data may comprise an image of an internal structure of a human eye.

The method may further comprise using the at least one hardware processor to, when the at least one classification is one of the one or more disorder classifications, use regression analysis to determine a severity of a disorder associated with the one disorder classification, wherein the report further indicates the determined severity of the disorder.

When the at least one classification is one of the one or more disorder classifications, the report may comprise one or more recommendations for treatment of a disorder associated with the one disorder classification. When the at least one classification is one of the one or more disorder classifications, the report may comprise an image from the ophthalmic image data that shows areas of importance used by the machine-learning classifier. The report may comprise probabilities of the plurality of classifications based on a Softmax function.

The method may further comprise using the at least one hardware processor to, after receiving the ophthalmic image data and before applying the machine-learning classifier: determining a type of the ophthalmic image data; and selecting the machine-learning classifier, that is associated with the determined type of the ophthalmic image data, from a plurality of different machine-learning classifiers associated with a plurality of different types of ophthalmic image data.

Applying the machine-learning classifier may comprise segmenting vessels in the ophthalmic image data using a U-net architecture. An activation function after each convolutional layer in the U-net architecture may comprise a rectifier linear unit (ReLU).

The ophthalmic image data may comprise video, wherein the method further comprises using the at least one hardware processor to, before applying the machine-learning classifier, stich a plurality of frames of the video together to generate a composite image to which the machine-learning classifier is applied.

The at least one hardware processor may be comprised within a server system, wherein receiving ophthalmic image data comprises receiving the ophthalmic image data over at least one network from a user device, and wherein providing a report comprises sending the report over the at least one network to the user device. The user device may be a mobile device.

The method may further comprise using at least one hardware processor in a mobile device to: when a connection to a remote server is available via at least one network, transmit the ophthalmic image data to the remote server for classification by a remote version of the machine-learning classifier; and, when no connection to the remote server is available, apply a local version of the machine-learning classifier to the ophthalmic image data. Receiving ophthalmic image data may comprise, at a mobile device, capturing ophthalmic image data using an ophthalmosocope that is detachably coupled to the mobile device.

The method may further comprise using the at least one hardware processor to generate a graphical user interface for a display of the mobile device, wherein the graphical user interface comprises one or more instructions for capturing the ophthalmic image data using the ophthalmoscope. The method may further comprise using the at least one hardware processor to train the machine-learning classifier to exhibit a sensitivity of at least 90% and a specificity of at least 90%. The method may further comprise using the at least one hardware processor to train the machine-learning classifier to exhibit an area under the curve (AUC) of at least 0.9. The method may further comprise using the at least one hardware processor to train the machine-learning classifier using a deep-learning procedure. The ophthalmic image data may comprise a retinal image. The ophthalmic image data may comprise a fundus image. The one or more disorder classifications may be a plurality of disorder classifications, wherein the plurality of disorder classifications further comprise at least one of a cataract, myopia, kidney disease, hypertension, or stroke.

In an embodiment, a system is disclosed that comprises: at least one hardware processor; and one or more software modules configured to, when executed by the at least one hardware processor, perform the methods above. The system may comprise an electronic kiosk comprising the at least one hardware processor and the one or more software modules. The electronic kiosk may comprise: an imaging component configured to capture the ophthalmic image data; and a head positioner, wherein the head positioner comprises a chin rest and a forehead rest configured to align a human eye with the imaging component.

In an embodiment, a non-transitory computer-readable medium having instructions stored thereon is disclosed, wherein the instructions, when executed by a processor, cause the processor to perform the methods above.

BRIEF DESCRIPTION OF THE DRAWINGS

The details of the disclosed embodiments, both as to structure and operation, may be gleaned in part by study of the accompanying drawings, in which like reference numerals refer to like parts, and in which.

DETAILED DESCRIPTION OF THE DISCLOSURE

Figure 1C:
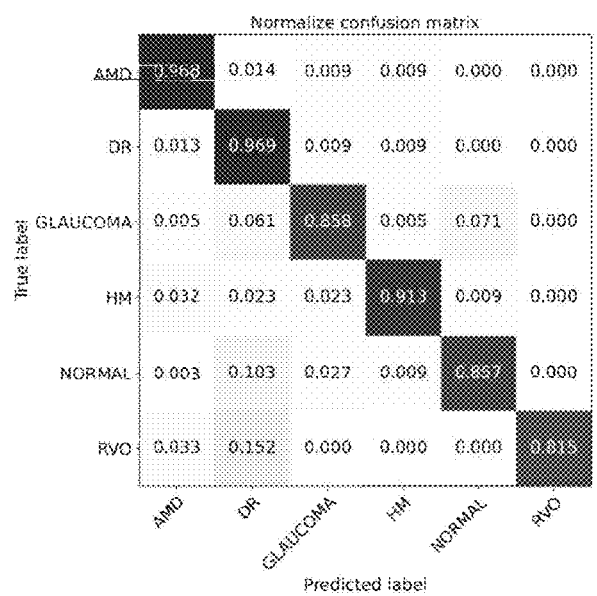
FIG. 1 shows a confusion matrix for a trained model validated using external validation sets including: A) Asian cohort; B) Caucasian cohort; C) Brazilian cohort; and D) Hand-held camera, according to an embodiment.

All publications, patents, and patent applications mentioned in this specification are herein incorporated by reference to the same extent as if each individual publication, patent, or patent application was specifically and individually indicated to be incorporated by reference.

Disclosed herein are systems, methods, and software for detecting eye diseases and systemic diseases based on imaging data. In some cases, disease detection is successfully performed in comparison to human clinicians, including when the analyzed images do not have pathological features that are detectable by humans. The advantages conferred by the present disclosure include the early detection of diseases or disorders when ophthalmic images such as retinal images do not display readily observable clinical features known to correspond to such diseases or disorders, for example, in the case of early stage or pre-disease status. As the cost to treat a blinding disease has proven to be more expensive than the cost to prevent its progression, earlier detection and treatment would relieve both the economic and personal burdens, while preventing an estimated 205.1 million individuals from progressing to moderate to severe blindness.

The present disclosure recognizes the potential for evaluating overall systemic health and disease status using information about the retina. Features such as retinal vessel caliber, tortuosity, arterial and vein crossing points, retinal microvascular changes, retinal hemorrhaging, and nerve fiber layer infarctions not only denote systemic manifestations of disease, but indicate other unique individual hallmarks, such as age and gender. Accordingly, disclosed herein are systems and methods for utilizing eye images as novel point-of-care biomarkers for systemic disease. One key advantage of this approach is that retinal image acquisition is non-invasive, easy to obtain, quick, and inexpensive with current technology.

While AI algorithms have advanced considerably in theory, their real-world implementation presents substantial challenges in practice, including data sharing and privacy issues, transparency and interpretability of algorithms, data standardization and interoperability across multiple platforms, and evolving regulatory paradigms. Additionally, in low-resource settings, one of the key challenges is the lack of stable computational infrastructure and the computational resources required to run these algorithms. In recognition of this limitation, disclosed herein are AI-based technologies on mobile platforms that empower users at the point of care such as patients or caregivers to diagnose or assess patient health. Additionally, high-quality retinal images can be reliably captured with low-cost smartphone attachments and therefore could deliver systemic and retinal health check-ups in regions experiencing avoidable blindness due to socioeconomic and geographic barriers.

In some aspects, the systems, methods, and software disclosed herein provide for the efficient and convenient access to the accurate disease detection processes described throughout the present disclosure. In some embodiments, the systems, methods, and software disclosed herein are implemented at the point of care such as in the case of smartphone integration for capturing and diagnosing various diseases. Low-resource settings shoulder a disproportionate share of the world's avoidable visual impairment due to the shortage of healthcare providers, a lack of healthcare infrastructure, and difficulty of patients in accessing health services due to geographic and socioeconomic barriers. Accordingly, the implementations disclosed herein offer an innovative solution that can be deployed to the point of care at the user or consumer level. Therefore, the systems and methods disclosed herein provide an especially valuable benefit in resource-poor countries like Nigeria where the physician to patient ratio is 1:2660 and smartphone ownership remains 1:3.5, which makes AI-based smartphone technology an applicable alternative to providing physician-based health care at the hands of the patient. In some instances, the requirement of the healthcare provider is reduced while empowering the patient to self-detect or diagnose. For example, the healthcare provider may provide remote monitoring, analysis, or confirmation of the device-based diagnosis at the point of care, thereby facilitating fast, efficient, and cheaper disease detection. Thus, integration of artificial intelligence as described herein provides an avenue to level the playing field of unequal access to early disease detection resources. By automating tasks or facilitating rapid diagnosis, artificial intelligence can promote access to health services, in particular within developing settings where the number of patients vastly exceeds the number of healthcare providers.

In some aspects, the systems, methods, and software disclosed herein provide an improvement in the field of software-based image data processing by leveraging machine learning approaches that offer superior performance metrics such as accuracy compared to human counterparts. In some embodiments, transfer learning using non-domain data is used to enhance the performance of the trained classifier. While artificial intelligence (AI) has the potential to revolutionize disease diagnosis in healthcare, clinical interpretability and actionable decision-making remain challenging. Accordingly, an AI system capable of mimicking the diagnostic decision-making process and facilitating referral tasks anywhere in the world would be highly beneficial for early detection and prevention of common diseases. Accordingly, embodiments of the systems, methods, and software described herein utilize deep learning techniques to diagnose common eye and systemic diseases.

In some aspects, the systems, methods, and software disclosed herein provide an improvement in the field of software-based image data processing whereby retinal images are used to detect or predict the development of an ophthalmic or systemic disease, disorder, or condition at a future time point. In some embodiments, retinal imaging allows for the detection of a pre-disease or early disease status. In some embodiments, retinal imaging allows for the detection of various stages of a disease, disorder, or condition such as, for example, moderate and severe non-proliferative stages and proliferative stages of diabetic retinopathy. The retinal image can be a simple image such as a fundus photograph or image. In some embodiments, the ophthalmic or retinal image used in the systems, methods, and software disclosed herein is not an optical coherence tomography (OCT) image. Accordingly, in some embodiments, a fundus image is analyzed or processed to obtain an accurate output.

In some embodiments, the present disclosure solves the technical problem of insufficient images in the relevant domain (e.g. medical images for a specific ophthalmic disease) for training algorithms to effectively perform image analysis and/or diagnosis. Certain embodiments of the present disclosure include systems and techniques applying a transfer learning algorithm to train an initial machine learning algorithm such as a convolutional neural network on images outside of the specific domain of interest to optimize the weights in the lower layer(s) for recognizing the structures found in the images. The weights for the lower layer(s) are then frozen, while the weights of the upper layer(s) are retrained using images from the relevant domain to identify output according to the desired diagnosis (e.g. identification or prediction of specific ophthalmic diseases or conditions). This approach allows the classifier to recognize distinguishing features of specific categories of images (e.g. images of the eye) far more quickly using significantly fewer training images and requiring substantially less computational power. The use of non-domain images to partially train or pre-train the classifier allows optimization of the weights of one or more of the neural network layers using a deep reservoir of available images corresponding to thousands of categories. The result is a classifier having a sensitivity, specificity, and accuracy that is unexpected and surprising compared to the traditional approach, especially in view of the improvements in speed, efficiency, and computational power required. Indeed, certain embodiments of the classifier outperform human experts in correctly diagnosing medical images according to sensitivity, specificity, accuracy, or a combination thereof.

Disclosed herein, in one aspect, is a computer-implemented method for analyzing ophthalmic imaging data obtained from a subject to determine the presence of an ophthalmic or systemic disease, disorder, or condition, the method comprising: a) obtaining the ophthalmic imaging data; and b) processing the ophthalmic imaging data with an algorithm comprising a classifier trained using a machine learning procedure to output a determination of the presence of the ophthalmic or systemic disease, disorder, or condition. In some embodiments, the determination has a sensitivity of at least 90% and a specificity of at least 90%. In some embodiments, the determination has an AUC of at least 0.9. In some embodiments, the machine learning procedure comprises training a model using a deep learning procedure to generate the classifier. In some embodiments, the classifier is a convolutional neural network. In some embodiments, the machine learning procedure comprises performing a transfer learning procedure to generate the classifier. In some embodiments, the transfer learning procedure comprises pre-training a neural network using non-domain images, freezing at least one feature layer of the neural network, and training the neural network using domain images. In some embodiments, the method further comprises making a medical treatment recommendation based on the determination. In some embodiments, the ophthalmic imaging data comprises an ophthalmic image. In some embodiments, the ophthalmic image is a retinal image. In some embodiments, the ophthalmic image is a fundus image. In some embodiments, the ophthalmic disease or disorder is selected from the group consisting of age-related macular degeneration, diabetic retinopathy, glaucoma, cataract, myopia, retinal vein occlusions, kidney disease, hypertension, and stroke. In some embodiments, the subject has not manifested visible abnormalities or symptoms of the ophthalmic or systemic disease, disorder, or condition at the time the ophthalmic imaging data was generated.

Disclosed herein, in another aspect, is a computer-implemented system configured for analyzing ophthalmic imaging data obtained from a subject to determine the presence of an ophthalmic or systemic disease, disorder, or condition, the system comprising: a) an electronic device comprising: a processor, a memory, a display, a camera, and an operating system configured to perform executable instructions; b) a computer program stored in the memory of the electronic device, the computer program including instructions executable by the user electronic device to create an application comprising: i) a software module obtaining the ophthalmic imaging data; and ii) a software module processing the ophthalmic imaging data with an algorithm comprising a classifier trained using a machine learning procedure to output a determination of the presence of the ophthalmic or systemic disease, disorder, or condition. In some embodiments, the determination has a sensitivity of at least 90% and a specificity of at least 90%. In some embodiments, the determination has an AUC of at least 0.9. In some embodiments, the machine learning procedure comprises training a model using a deep learning procedure to generate the classifier. In some embodiments, the classifier is a convolutional neural network. In some embodiments, the machine learning procedure comprises performing a transfer learning procedure to generate the classifier. In some embodiments, the transfer learning procedure comprises pre-training a neural network using non-domain images, freezing at least one feature layer of the neural network, and training the neural network using domain images. In some embodiments, the application further comprises a software module making a medical treatment recommendation based on the determination. In some embodiments, the ophthalmic imaging data comprises an ophthalmic image. In some embodiments, the ophthalmic image is a retinal image. In some embodiments, the ophthalmic image is a fundus image. In some embodiments, the ophthalmic disease or disorder is selected from the group consisting of age-related macular degeneration, diabetic retinopathy, glaucoma, cataract, myopia, retinal vein occlusions, kidney disease, hypertension, and stroke. In some embodiments, the subject has not manifested visible abnormalities or symptoms of the ophthalmic or systemic disease, disorder, or condition at the time the ophthalmic imaging data was generated.

In another aspect, disclosed herein is a non-transitory computer-readable medium comprising machine-executable code that, upon execution by one or more computer processors, implements a method for processing ophthalmic imaging data, the method comprising: a) obtaining the ophthalmic imaging data; and b) processing the ophthalmic imaging data with an algorithm comprising a classifier trained using a machine learning procedure to output a determination of the presence of the ophthalmic or systemic disease, disorder, or condition. In some embodiments, the determination has a sensitivity of at least 90% and a specificity of at least 90%. In some embodiments, the determination has an AUC of at least 0.9. In some embodiments, the machine learning procedure comprises training a model using a deep learning procedure to generate the classifier. In some embodiments, the classifier is a convolutional neural network. In some embodiments, the machine learning procedure comprises performing a transfer learning procedure to generate the classifier. In some embodiments, the transfer learning procedure comprises pre-training a neural network using non-domain images, freezing at least one feature layer of the neural network, and training the neural network using domain images. In some embodiments, the application further comprises a software module making a medical treatment recommendation based on the determination. In some embodiments, the ophthalmic imaging data comprises an ophthalmic image. In some embodiments, the ophthalmic image is a retinal image. In some embodiments, the ophthalmic image is a fundus image. In some embodiments, the ophthalmic disease or disorder is selected from the group consisting of age-related macular degeneration, diabetic retinopathy, glaucoma, cataract, myopia, retinal vein occlusions, kidney disease, hypertension, and stroke. In some embodiments, the subject has not manifested visible abnormalities or symptoms of the ophthalmic or systemic disease, disorder, or condition at the time the ophthalmic imaging data was generated.

In another aspect, disclosed herein is a computer-implemented system comprising: a) an electronic device comprising: a processor, a memory, a display, a camera, and an operating system configured to perform executable instructions; b) a portable device comprising an imaging component, said portable device configured to receive and position the electronic device to align the camera with the imaging component for capturing ophthalmic imaging data; and c) a computer program stored in the memory of the electronic device, the computer program including instructions executable by the user electronic device to create an application comprising: i) a software module obtaining the ophthalmic imaging data; and ii) a software module processing the ophthalmic imaging data with an algorithm comprising a classifier trained using a machine learning procedure to output a determination of a presence of an ophthalmic or systemic disease, disorder, or condition. In some embodiments, processing the ophthalmic imaging data comprises uploading the ophthalmic image or video to a cloud network to be analyzed by the trained classifier. In some embodiments, the ophthalmic imaging data comprises a retinal image or video captured by the electronic device using the portable device comprising the imaging component. In some embodiments, the determination has a sensitivity of at least 90% and a specificity of at least 90%. In some embodiments, the determination has an AUC of at least 0.9. In some embodiments, the machine learning procedure comprises training a model using a deep learning procedure to generate the classifier. In some embodiments, the classifier is a convolutional neural network. In some embodiments, the machine learning procedure comprises performing a transfer learning procedure to generate the classifier. In some embodiments, the transfer learning procedure comprises pre-training a neural network using non-domain images, freezing at least one feature layer of the neural network, and training the neural network using domain images. In some embodiments, the application further comprises a software module making a medical treatment recommendation based on the determination. In some embodiments, the ophthalmic imaging data comprises an ophthalmic image. In some embodiments, the ophthalmic image is a retinal image. In some embodiments, the ophthalmic image is a fundus image. In some embodiments, the ophthalmic disease or disorder is selected from the group consisting of age-related macular degeneration, diabetic retinopathy, glaucoma, cataract, myopia, retinal vein occlusions, kidney disease, hypertension, and stroke. In some embodiments, the subject has not manifested visible abnormalities or symptoms of the ophthalmic or systemic disease, disorder, or condition at the time the ophthalmic imaging data was generated. In some embodiments, the imaging component is an ophthalmoscope enabling the camera to capture the ophthalmic image or video from an eye of a subject. In some embodiments, the portable device comprises an adaptor configured to receive and position the electronic device. In some embodiments, the electronic device is a smartphone or a tablet.

In another aspect, disclosed herein is a computer-implemented system comprising: a) a medical imaging device configured to capture an ophthalmic image of a subject; b) an electronic device operatively coupled to the medical imaging device, comprising: a processor, a memory, a display, and an operating system configured to perform executable instructions; c) a computer program stored in the memory of the electronic device, the computer program including instructions executable by the user electronic device to create an application comprising: i) a software module obtaining the ophthalmic imaging data; and ii) a software module processing the ophthalmic imaging data with an algorithm comprising a classifier trained using a machine learning procedure to output a determination of a presence of an ophthalmic or systemic disease, disorder, or condition. In some embodiments, processing the ophthalmic imaging data comprises uploading the ophthalmic image or video to a cloud network to be analyzed by the trained classifier. In some embodiments, the determination has a sensitivity of at least 90% and a specificity of at least 90%. In some embodiments, the determination has an AUC of at least 0.9. In some embodiments, the machine learning procedure comprises training a model using a deep learning procedure to generate the classifier. In some embodiments, the classifier is a convolutional neural network. In some embodiments, the machine learning procedure comprises performing a transfer learning procedure to generate the classifier. In some embodiments, the transfer learning procedure comprises pre-training a neural network using non-domain images, freezing at least one feature layer of the neural network, and training the neural network using domain images. In some embodiments, the application further comprises a software module making a medical treatment recommendation based on the determination. In some embodiments, the ophthalmic imaging data comprises an ophthalmic image. In some embodiments, the ophthalmic image is a retinal image. In some embodiments, the ophthalmic image is a fundus image. In some embodiments, the ophthalmic disease or disorder is selected from the group consisting of age-related macular degeneration, diabetic retinopathy, glaucoma, cataract, myopia, retinal vein occlusions, kidney disease, hypertension, and stroke. In some embodiments, the subject has not manifested visible abnormalities or symptoms of the ophthalmic or systemic disease, disorder, or condition at the time the ophthalmic imaging data was generated. In some embodiments, the medical imaging device comprises an ophthalmoscope and a fundus camera. In some embodiments, the portable device comprises an adaptor configured to receive and position the electronic device. In some embodiments, the electronic device is a smartphone or a tablet. In some embodiments, the system is configured as a self-service kiosk. In some embodiments, the kiosk comprises a positioning component for positioning a head of a subject in front of the medical imaging device to capture the ophthalmic image. In some embodiments, the positioning component is configured to reduce or minimize head tilt by the subject. In some embodiments, the kiosk further comprises a microphone and a speaker, and is configured to provide teleconferencing with a remote healthcare provider to discuss the determination and optionally a treatment recommendation. In some embodiments, the kiosk comprises an interface for receiving payment information. In some embodiments, the interface comprises a card reader, a scanner, an RFID system, a cash acceptor, a touchscreen for entering payment information, or a combination thereof.

Disclosed herein, in another aspect, is a computer-implemented method for analyzing a fundus image obtained from a subject to determine the presence of an ophthalmic or systemic disease or disorder, the method comprising: a) obtaining the fundus image; and b) processing the fundus image with an algorithm comprising a classifier trained using a machine learning procedure to output a determination of the presence of the ophthalmic or systemic disease or disorder, wherein the subject does not exhibit visible abnormalities or symptoms of the ophthalmic or systemic disease or disorder.

Disclosed herein, in another aspect, is a computer-implemented system configured for analyzing a fundus image obtained from a subject to determine the presence of an ophthalmic or systemic disease or disorder, the system comprising: a) an electronic device comprising: a processor, a memory, a display, a camera, and an operating system configured to perform executable instructions; b) a computer program stored in the memory of the electronic device, the computer program including instructions executable by the user electronic device to create an application comprising: i) a software module obtaining the fundus image; and ii) a software module processing the fundus image with an algorithm comprising a classifier trained using a machine learning procedure to output a determination of the presence of the ophthalmic or systemic disease or disorder.

Disclosed herein, in another aspect, is a non-transitory computer-readable medium comprising machine-executable code that, upon execution by one or more computer processors, implements a method for processing a fundus image, the method comprising: a) obtaining the fundus image; and b) processing the fundus image with an algorithm comprising a classifier trained using a machine learning procedure to output a determination of the presence of the ophthalmic or systemic disease or disorder.

Disclosed herein, in another aspect, is a computer-implemented system comprising: a) an electronic device comprising: a processor, a memory, a display, a camera, and an operating system configured to perform executable instructions; b) a portable device comprising an imaging component, said portable device configured to receive and position the electronic device to align the camera with the imaging component for capturing a fundus image; and c) a computer program stored in the memory of the electronic device, the computer program including instructions executable by the user electronic device to create an application comprising: i) a software module obtaining the fundus image; and ii) a software module processing the fundus image with an algorithm comprising a classifier trained using a machine learning procedure to output a determination of a presence of an ophthalmic or systemic disease or disorder.

Disclosed herein, in another aspect, is a computer-implemented system comprising: a) a medical imaging device configured to capture a fundus image of an eye of a subject; b) an electronic device operatively coupled to the medical imaging device, comprising: a processor, a memory, a display, and an operating system configured to perform executable instructions; c) a computer program stored in the memory of the electronic device, the computer program including instructions executable by the user electronic device to create an application comprising: i) a software module obtaining the fundus image; and ii) a software module processing the fundus image with an algorithm comprising a classifier trained using a machine learning procedure to output a determination of a presence of an ophthalmic or systemic disease or disorder.

It is recognized that implementation of clinical decision support algorithms for medical imaging with improved reliability and clinical interpretability can be achieved through one or combinations of technical features of the present disclosure. According to some aspects, disclosed herein is a diagnostic tool for identifying common ophthalmic diseases and/or systemic diseases. In some embodiments, a machine learning framework is implemented to carry out the diagnosis. Examples of the machine learning framework include deep learning models such as artificial neural networks. Certain embodiments of the disclosed framework implement a transfer learning algorithm, which allows for the training of a highly accurate neural network with a fraction of the data required in more conventional approaches. In some embodiments, the model disclosed herein is applied towards medical data such as medical images of the eye to identify or diagnose common ophthalmic diseases and/or systemic diseases. In some embodiments, the algorithm(s) and/or model(s) disclosed herein are implemented on various computing devices such as at the point of care, thereby enabling users and patients to self-diagnose. Examples of the computing devices include portable communication devices such as smart phones optionally coupled to specialized portable imaging devices, digital processing devices operably coupled to imaging devices, specialized diagnostic devices such as kiosks, and other implementations.

In certain embodiments, the machine learning approach disclosed herein is applied to a large and clinically heterogeneous dataset of ophthalmic images such as fundus images and is capable of achieving diagnostic performance that is comparable to or superior to that of human experts in classifying ophthalmic diseases or systemic diseases. As used herein, a "disease" can refer to disease and additionally disorders and/or conditions. Examples of ophthalmic diseases include macular degeneration, diabetic retinopathy, glaucoma, cataract, myopia, and retinal vein occlusions. Examples of systemic diseases include diabetes and its kidney disease, hypertension and stroke. Furthermore, certain embodiments of the transfer learning approach scales with additional training images and development of clinical imaging datasets as well as with continuing advancements in the field of convolutional neural networks (CNN) and image processing. In some embodiments, provided herein is a platform that interfaces with web and/or mobile applications that upload OCT images for remote diagnosis with high accuracy. The algorithm not only demonstrates strong performance for various ophthalmic diseases, but also holds broad clinical utility for image-based diagnosis of systemic diseases.

In some embodiments, the machine learning frameworks disclosed herein utilize deep learning neural networks (DNNs) that provide a revolutionary step forward in machine learning technique that enable the classification of an image such as a fundus photograph in significantly less time than a human.

In some embodiments, the systems and methods disclosed herein diagnose a range of common blinding diseases such as AMD, DR, HM, RVO, glaucoma, cataracts, and normal retinas. In some embodiments, disclosed herein is a model that shows high accuracy amongst all disease phenotypes, including in different cohorts such as in China, US, and Brazil, as well as handheld cohorts. In some embodiments, the model is able to diagnose or differentiate diabetic patients without retinopathy from non-diabetic patients with normal retinas. In some embodiments, the model is able to detect underlying systemic complications by distinguishing diabetic patients with diabetic kidney disease from diabetic patients without any known complications. In some embodiments, the model demonstrates high accuracy in detecting unique patient characteristics such as age, gender, blood pressure and stroke. In some embodiments, these techniques serve as non-invasive screening tools as part of a health check-up or medical screening.

Artificial intelligence (AI) is poised to become a transformational force in the field of healthcare. From diagnosing chronic systemic diseases, to interpreting radiographic images, to identifying cancer, there are nearly endless opportunities that leverage technology to produce more efficient, precise, and impactful answers and interventions to improve patient care. A key challenge, however, is the need for accurate and applicable training that requires tens of thousands of images from diverse patient populations, different clinical sites, different cameras, and different photographers.

The systems and methods show high applicability among a wide array of different geographic populations as demonstrated by the accuracy level when applied to a Brazilian population, which is known to be highly heterogeneous, comprising African, European, and indigenous descendents.

In addition, in some embodiments, the systems and methods provide high accuracy with wide applicability across different funduscopic devices, different ophthalmologic centers, and different ethnic cohorts, and can therefore serve as effective screening tool for both retinal diseases and systemic indications.

In some embodiments, disclosed herein are systems and methods configured to provide a health screening comprising obtaining a retinal image, and evaluating the retinal image for a plurality of diseases or conditions. In some embodiments, the plurality of diseases or conditions comprises ophthalmic diseases or conditions. In some embodiments, the plurality of diseases or conditions comprises systemic diseases or conditions. In some embodiments, the plurality of diseases or conditions comprises both ophthalmic and systemic diseases and/or conditions. In some embodiments, the systemic diseases or conditions are not traditionally diagnosed or detected using retinal imaging, thus presenting a novel and unconventional diagnostic or screening technique.

In some embodiments, disclosed herein are smartphone applications (e.g., iOS application) and fundoscopy attachments that together provide expert care to rural communities and third world regions such as South Asia, South America, and Sub-Saharan Africa, where often the most preventable cases of blinding eye diseases occur. Even in developed countries like the United States, studies have cited ethnic minorities and low socioeconomic status as high-risk factors for visual impairment with trust, transportation, and cost frequently reported as significant health-care burdens. However, as mentioned above, the cost to treat blinding diseases has proven to be more expensive than the cost to prevent their progression. The economic burden of visual impairment in 2012 was 27.5 billion US dollars, with 215,000 quality-adjusted life years lost. Such costs include visual aids, diagnostics, productivity loss, and caregiver fees. Therefore, providing an accessible and affordable eye-care checkup system, as disclosed herein, could potentially relieve economic and health-care burdens at both individual and institutional levels. Such systems therefore have the potential to significantly improve upon traditional disease screening programs.

In some embodiments, automated recognition systems are developed using a limited amount of image data. With the advent of smartphones and digital cameras, the growth in image data has been exponential. This explosion of data and its widespread availability on the web have led to a need for effective methods for analyzing the huge amount of data efficiently without time-consuming and complex steps. As disclosed herein, DNNs make it possible to analyze the large amount of data currently being generated, and likewise, the large amount of data make it possible for DNNs to be well trained.

As disclosed herein, in certain embodiments, convolutional neural network (CNN) layers allow for significant gains in the ability to classify images and detect objects in a picture. In various embodiments, CNNs are composed of multiple processing layers to which image analysis filters, or convolutions, are applied. In some embodiments, the abstracted representation of images within each layer is constructed by systematically convolving multiple filters across the image, producing a feature map which is used as input to the following layer. CNNs learn representations of images with multiple levels of increasing understanding of the image contents, which is what makes the networks deep. This deep learning method is capable of discovering intricate structures in large data sets by using the backpropagation learning algorithm to change its internal parameters to minimize errors in making the desired classification. Each layer is increasingly sophisticated in its representation of the organization of the data compared to the previous layer. The first few layers of the neural network can extract simple structures, such as lines and edges, while the layers up the chain begin to determine more complex structures. This architecture makes it possible to process images in the form of pixels as input and to give the desired classification as output. Accordingly, in certain embodiments, the image-to-classification approach in one classifier replaces the multiple steps of previous image analysis methods. As a result, the CNNs disclosed herein dramatically improve the state-of-the-art in visual object recognition.

Within ophthalmology, the relatively small amount of image data may be insufficient to train the potentially tens of millions of parameters in a modern DNN. Accordingly, disclosed herein are methods of detecting ophthalmic and/or systemic diseases that address a lack of data in the relevant domain by leveraging data from a similar domain. For example, a large database of labeled images has been collected and made available as ImageNet with 1,000 object categories. In certain embodiments, a CNN is first trained on this dataset to develop features at its lower layers that are important for discriminating objects. In further embodiments, a second network is created that copies the parameters and structure of the first network, but with the final layer(s) optionally re-structured as needed for a new task. In certain embodiments, these final layer(s) are configured to perform the classification of retinal images. Thus, in some embodiments, the second network uses the first network to seed its structure. This allows training to continue on the new, but related task. In some embodiments, the first network is trained using labeled images comprising non-domain images (e.g. images not labeled with the final desired classification such as glaucoma), and the second network is trained using labeled images comprising domain images (e.g. images classified as having or not having glaucoma) to complete the training, allowing for high accuracy diagnosis of ophthalmic disorders and/or conditions. The method of transferring general classification knowledge from one domain to another is called transfer learning. As disclosed herein, the application of transfer learning within the field of machine learning-based diagnosis of ophthalmic diseases and conditions has proven to be a highly effective technique, particularly when faced with domains with limited data. By retraining a model with weights already optimized to recognize the features of standard objects rather than training a completely blank network, the model or classifier can recognize the distinguishing features of images much faster and with significantly fewer training examples.

Medical Imaging

In certain aspects, the machine learning framework disclosed herein is used for analyzing medical imaging data. In some embodiments, the medical imaging data comprises ophthalmic images, which can include images of the internal structure of the eye such as the retina and/or retinal vasculature, macula, and optic nerve. The framework described herein is applicable to various types of medical imaging including ophthalmic imaging. Ophthalmic imaging is a type of medical imaging that scans or captures one or more structures of the eye. In some embodiments, the machine learning framework is used to analyze ophthalmic images generated using at least one ophthalmic medical imaging technique selected from optical coherence tomography (OCT), color fundus photography of the retina (CFP), corneal topography, slit-lamp photography, fluorescein angiography, indocyanine green angiography, fundus auto-fluorescence, optic nerve head analysis, endothelial cell-layer imaging, and external imaging. In some embodiments, ophthalmic images are generated using specialized imaging equipment. However, the requirement of specialized imaging equipment can increase the burden of obtaining a diagnosis, especially in low-income and/or underdeveloped areas. Accordingly, in some instances, non-specialized imaging can be utilized to provide accurate detection or one or more ophthalmic or systemic diseases or disorders. For example, fundus imaging of the retina using an ophthalmoscope and a standard digital camera such as in a smart phone can be implemented to perform the analysis described herein to obtain detection or diagnosis or a disease or disorder. In some embodiments, a digital retinal camera is used for color fundus photography and/or fluorescein angiography. In some embodiments, an optical coherence tomography enables cross-sectional imaging of the retina such as for macular and optic nerve head imaging. In some embodiments, a scanning laser ophthalmoscope is used for fundus autofluorescence, fluorescein angiography and indocyanine green angiography. In some embodiments, photo slit-lamp micrography is used to photograph anterior eye structures (e.g. cornea, iris, conjunctiva, and lens). In some embodiments, corneal topography is used to measure the thickness, refractive power, and shape of the cornea. In some embodiments, an optic nerve head analyzer is used for optic nerve head imaging. In some embodiments, external photography is used to image the exterior of the eye, eyelid, or other structures in proximity to the eye. In some embodiments, a Rostock corneal module (RCM) is used to generate high-magnification images of the corneal layers, which allows counting of endothelial cells.

A lack of sufficient suitable medical images or medical imaging data can lead to inaccurate or poorly trained classifiers. However, embodiments of the systems, methods, and devices disclosed herein implement transfer learning to improve the training of models using images or imaging data that is not suitable for directly training the classifier. In some embodiments, a model is trained during a first step using non-medical images. In some embodiments, transfer learning is implemented to further train a model on suitable medical images (e.g., retinal images labeled with associated diagnostic outcomes). By leveraging non-domain images for part of the training, a trained model or classifier can be generated that provides improved predictive accuracy compared to a model trained using only the available labeled images.

In some embodiments, the algorithms disclosed herein, such as machine learning algorithms, use transfer learning. In some embodiments, the algorithms disclosed herein use non-domain images to pre-train a model or classifier. In some embodiments, the algorithms disclosed herein that utilize a transfer learning procedure using non-domain images achieve at least one performance metric (e.g., an accuracy, sensitivity, specificity, AUC, positive predictive value, negative predictive value, or any combination thereof) for an independent data set (e.g., test dataset not used in training) that is at least 80%, 85%, 90%, 95%, 96%, 97%, 98%, or at least 99% similar to an algorithm that is trained using the medical images alone. In some embodiments, the similar performance metric is obtained when the transfer learning procedure and the non-transfer learning procedure utilize the same set of labeled images for training.

In some embodiments, a machine learning algorithm or model is pre-trained using non-domain images numbering about 1,000 to about 300,000. In some embodiments, a machine learning algorithm or model is pre-trained using non-domain images numbering at least about 1,000. In some embodiments, a machine learning algorithm or model is pre-trained using non-domain images numbering at most about 300,000. In some embodiments, a machine learning algorithm or model is pre-trained using non-domain images numbering about 1,000 to about 2,000, about 1,000 to about 5,000, about 1,000 to about 10,000, about 1,000 to about 15,000, about 1,000 to about 20,000, about 1,000 to about 30,000, about 1,000 to about 40,000, about 1,000 to about 50,000, about 1,000 to about 100,000, about 1,000 to about 200,000, about 1,000 to about 300,000, about 2,000 to about 5,000, about 2,000 to about 10,000, about 2,000 to about 15,000, about 2,000 to about 20,000, about 2,000 to about 30,000, about 2,000 to about 40,000, about 2,000 to about 50,000, about 2,000 to about 100,000, about 2,000 to about 200,000, about 2,000 to about 300,000, about 5,000 to about 10,000, about 5,000 to about 15,000, about 5,000 to about 20,000, about 5,000 to about 30,000, about 5,000 to about 40,000, about 5,000 to about 50,000, about 5,000 to about 100,000, about 5,000 to about 200,000, about 5,000 to about 300,000, about 10,000 to about 15,000, about 10,000 to about 20,000, about 10,000 to about 30,000, about 10,000 to about 40,000, about 10,000 to about 50,000, about 10,000 to about 100,000, about 10,000 to about 200,000, about 10,000 to about 300,000, about 15,000 to about 20,000, about 15,000 to about 30,000, about 15,000 to about 40,000, about 15,000 to about 50,000, about 15,000 to about 100,000, about 15,000 to about 200,000, about 15,000 to about 300,000, about 20,000 to about 30,000, about 20,000 to about 40,000, about 20,000 to about 50,000, about 20,000 to about 100,000, about 20,000 to about 200,000, about 20,000 to about 300,000, about 30,000 to about 40,000, about 30,000 to about 50,000, about 30,000 to about 100,000, about 30,000 to about 200,000, about 30,000 to about 300,000, about 40,000 to about 50,000, about 40,000 to about 100,000, about 40,000 to about 200,000, about 40,000 to about 300,000, about 50,000 to about 100,000, about 50,000 to about 200,000, about 50,000 to about 300,000, about 100,000 to about 200,000, about 100,000 to about 300,000, or about 200,000 to about 300,000. In some embodiments, a machine learning algorithm or model is pre-trained using non-medical images numbering about 1,000, about 2,000, about 5,000, about 10,000, about 15,000, about 20,000, about 30,000, about 40,000, about 50,000, about 100,000, about 200,000, or about 300,000.

In some embodiments, a machine learning algorithm or model is trained using labeled images numbering about 50 to about 50,000. In some embodiments, a machine learning algorithm or model is trained using labeled images numbering at least about 50. In some embodiments, a machine learning algorithm or model is trained using labeled images numbering at most about 50,000. In some embodiments, a machine learning algorithm or model is trained using labeled images numbering about 50 to about 100, about 50 to about 200, about 50 to about 300, about 50 to about 400, about 50 to about 500, about 50 to about 1,000, about 50 to about 5,000, about 50 to about 10,000, about 50 to about 20,000, about 50 to about 30,000, about 50 to about 50,000, about 100 to about 200, about 100 to about 300, about 100 to about 400, about 100 to about 500, about 100 to about 1,000, about 100 to about 5,000, about 100 to about 10,000, about 100 to about 20,000, about 100 to about 30,000, about 100 to about 50,000, about 200 to about 300, about 200 to about 400, about 200 to about 500, about 200 to about 1,000, about 200 to about 5,000, about 200 to about 10,000, about 200 to about 20,000, about 200 to about 30,000, about 200 to about 50,000, about 300 to about 400, about 300 to about 500, about 300 to about 1,000, about 300 to about 5,000, about 300 to about 10,000, about 300 to about 20,000, about 300 to about 30,000, about 300 to about 50,000, about 400 to about 500, about 400 to about 1,000, about 400 to about 5,000, about 400 to about 10,000, about 400 to about 20,000, about 400 to about 30,000, about 400 to about 50,000, about 500 to about 1,000, about 500 to about 5,000, about 500 to about 10,000, about 500 to about 20,000, about 500 to about 30,000, about 500 to about 50,000, about 1,000 to about 5,000, about 1,000 to about 10,000, about 1,000 to about 20,000, about 1,000 to about 30,000, about 1,000 to about 50,000, about 5,000 to about 10,000, about 5,000 to about 20,000, about 5,000 to about 30,000, about 5,000 to about 50,000, about 10,000 to about 20,000, about 10,000 to about 30,000, about 10,000 to about 50,000, about 20,000 to about 30,000, about 20,000 to about 50,000, or about 30,000 to about 50,000. In some embodiments, a machine learning algorithm or model is trained using labeled images numbering about 50, about 100, about 200, about 300, about 400, about 500, about 1,000, about 5,000, about 10,000, about 20,000, about 30,000, or about 50,000.

Machine Learning

Disclosed herein, in various embodiments, are machine learning methods for analyzing medical data including, for example, ophthalmic images and eye-related data. In an exemplary embodiment, the machine learning framework disclosed herein is used for analyzing images of the retina (e.g., fundus images) for the diagnosis of ophthalmic and/or systemic diseases or conditions. In some embodiments, the predictions or diagnoses generated according to the systems, methods, and devices described herein include detection or diagnosis of an ophthalmic or systemic disease, disorder, or condition. In some embodiments, the predictions or diagnoses include evaluation of risk or likelihood of an ophthalmic or systemic disease, disorder, or condition. In some embodiments, the predictions or diagnosis comprise a category or classification of an ophthalmic or systemic disease, disorder, or condition.

In various embodiments, medical imaging is used for carrying out predictions or diagnoses described herein. Examples of medical imaging include fundus photographs that can be obtained using fundus cameras that utilize a specialized microscope (e.g., an ophthalmoscope. The prevalence of fundus photography makes it particularly suitable for the rapid and accurate diagnostic screening for ophthalmic and/or systemic diseases. This is particularly relevant in areas without easy access to specialized physicians, such as rural areas or developingll ow-income settings, Delays in diagnosis and/or treatment could result in severe consequences impacting health and long-term prognosis. It is recognized in the present disclosure that one solution is to implement computational decision support algorithms for interpretation of medical imaging such as fundus images.

Disclosed herein, in various aspects, are methods incorporating machine learning techniques (e.g. deep learning utilizing convolutional neural networks) that demonstrate great diagnostic power using retinal imagery that leverages databases of retinal images including public databases. Conventional approaches in computer vision using deep learning in other medical fields have encountered significant challenges due to the unavailability of large datasets of labeled medical imagery. Disclosed herein are methods that solve these challenges using innovative methods such as the application of transfer learning.

Accordingly, in some embodiments, provided herein is an AI transfer learning framework for the diagnosis of common sight-threatening retinal diseases with a dataset of retinal images (e.g., fundus photographs) that is capable of achieving highly accurate diagnosis comparable to human expert performance. In some embodiments, this AI framework categorizes images and generates a corresponding priority or label for the classification such as "urgent referrals" or "routine referrals." In some embodiments, normal images are labeled for "observation." Thus, certain embodiments of the present disclosure utilize the AI framework as a triage system to generate a referral, mimicking real-world applications in community settings, primary care, and urgent care clinics. These embodiments may ultimately confer broad public health impact by promoting earlier diagnosis and detection of disease progression, thereby facilitating treatment that can improve visual outcomes and quality of life.

In certain aspects, disclosed herein are machine learning frameworks for generating models or classifiers that diagnose one or more ophthalmic or systemic diseases, disorders, or conditions. These models or classifiers can be implemented in any of the systems or devices disclosed herein such as diagnostic kiosks or portable devices such as smartphones with attachable imaging devices (e.g., ophthalmoscopes). Non-classifier regression models are also contemplated for any of the methods described herein. For example, regression analysis can be performed to generate an output indicative of a severity of an ophthalmic or systemic disease or disorder.

In some embodiments, the classifier exhibits performance metrics such as accuracy, sensitivity, specificity, positive predictive value, negative predictive value, and/or area under the curve (AUC) for an independent sample set. In some embodiments, the classifier exhibits performance metrics such as higher accuracy, sensitivity, specificity, positive predictive value, negative predictive value, and/or AUC for an independent sample set compared to an average human clinician (e.g. an average ophthalmologist). In some embodiments, the classifier provides an accuracy of at least 70%, at least 75%, at least 80%, at least 85%, at least 90%, at least 91%, at least 92%, at least 93%, at least 94%, at least 95%, at least 96%, at least 97%, at least 98%, or at least 99% when tested against at least 100, 200, 300, 400, 500, 600, 700, 800, 900, or 1000 independent samples (e.g., images). In some embodiments, the classifier provides a sensitivity (true positive rate) of at least 70%, at least 75%, at least 80%, at least 85%, at least 90%, at least 91%, at least 92%, at least 93%, at least 94%, at least 95%, at least 96%, at least 97%, at least 98%, at least 99%, and/or a specificity (true negative rate) of at least 70%, at least 75%, at least 80%, at least 85%, at least 90%, at least 91%, at least 92%, at least 93%, at least 94%, at least 95%, at least 96%, at least 97%, at least 98%, or at least 99% when tested against at least 100, 200, 300, 400, 500, 600, 700, 800, 900, or 1000 independent samples (e.g. images). In some embodiments, the classifier provides a positive predictive value (PPV) of at least 70%, at least 75%, at least 80%, at least 85%, at least 90%, at least 91%, at least 92%, at least 93%, at least 94%, at least 95%, at least 96%, at least 97%, at least 98%, or at least 99% when tested against at least 100, 200, 300, 400, 500, 600, 700, 800, 900, or 1,000 independent samples. In some embodiments, the classifier provides a negative predictive value (NPV) of at least 70%, at least 75%, at least 80%, at least 85%, at least 90%, at least 91%, at least 92%, at least 93%, at least 94%, at least 95%, at least 96%, at least 97%, at least 98%, or at least 99% when tested against at least 100, 200, 300, 400, 500, 600, 700, 800, 900, or 1,000 independent samples. In some embodiments, the classifier has an AUC of at least 0.7, 0.75, 0.8, 0.85, 0.9, 0.91, 0.92, 0.93, 0.94, 0.95, 0.96, 0.97, 0.98 or 0.99 when tested against at least 100, 200, 300, 400, 500, 600, 700, 800, 900, or 1000 independent samples (e.g. retinal images). In some embodiments, the classifier has a weighted error compared to one or more independent experts of no more than 20%, no more than 15%, no more than 12%, no more than 10%, no more than 9%, no more than 8%, no more than 7%, no more than 6%, no more than 5%, no more than 4%, no more than 3%, no more than 2%, or no more than 1% when tested against at least 100, 200, 300, 400, 500, 600, 700, 800, 900, or 1,000 independent samples.

In some embodiments, the machine learning algorithm comprises a neural network. In some embodiments, the neural network comprises at least 1, at least 2, at least 3, at least 4, at least 5, at least 6, at least 7, at least 8, at least 9, at least 10, at least 15, at least 20, at least 25, at least 30, at least 40, at least 50, at least 60, at least 70, at least 80, at least 90, at least 100, at least 150, at least 200, at least 250, at least 300, at least 350, at least 400, at least 450, at least 500, at least 600, at least 700, at least 800, at least 900, at least 1000, at least 5000, or at least 10000 or more neurons or nodes and/or no more than 2, no more than 3, no more than 4, no more than 5, no more than 6, no more than 7, no more than 8, no more than 9, no more than 10, no more than 15, no more than 20, no more than 25, no more than 30, no more than 40, no more than 50, no more than 60, no more than 70, no more than 80, no more than 90, no more than 100, no more than 150, no more than 200, no more than 250, no more than 300, no more than 350, no more than 400, no more than 450, no more than 500, no more than 600, no more than 700, no more than 800, no more than 900, no more than 1000, no more than 5000, or no more than 10000 neurons or nodes. In some embodiments, the number of neurons is limited to below a threshold number in order to prevent overfitting. In some embodiments, the number of neurons is no more than 5, 6, 7, 8, 9, or 10 neurons.

Although transfer learning allows the training of a highly accurate model with a relatively small training dataset, its performance would be inferior to that of a model trained from a random initialization on an extremely large dataset of fundus images, since even the internal weights can be directly optimized for fundus feature detection. However, transfer learning using a pre-trained model trained on millions of various medical images can generate a more accurate model when retraining layers for other medical classifications.

The performance of a model can depend highly on the weights of the pre-trained model. Therefore, in some embodiments, the performance of this model is enhanced when tested on a larger ImageNet dataset with more advanced deep learning techniques and architecture described herein. Further, in certain embodiments, the performance of this approach is improved by incorporating ongoing developments in the field of convolutional neural networks applied outside of medical imaging.

In some embodiments, fundus imaging is used as a demonstration of a generalized approach in medical image interpretation and subsequent decision making. The disclosed framework identified potential pathology on a tissue map to make a referral decision with performance comparable to human experts, enabling timely diagnose of the two most common causes of irreversible severe vision loss. In some embodiments, the systems, methods, and devices disclosed herein provide one or more treatment recommendations in addition to a diagnosis or detection of an ophthalmic or systemic disease or condition. Laser surgery can help seal off leaking blood vessels to reduce retinal swelling. In severe cases of ophthalmic disorders or conditions (e.g., advanced diabetic retinopathy), a vitrectomy may be recommended or performed to remove vitreous gel and blood from leaking vessels (and optional removal of scar tissue) to restore or improve visual acuity. In some embodiments, the treatment recommendation comprises lifestyle advice such as methods for managing blood sugar through diet, exercise, medicine, and other factors. In some embodiments, the treatment recommendation further comprises information relating to one or more healthcare providers suitable for providing the recommended treatment. In some embodiments, the one or more healthcare providers are selected based on location proximity to the location of the user and/or the system or device providing the recommendation. In some embodiments, the healthcare providers are selected based on available resources for providing the recommended treatment. In some embodiments, additional information for the healthcare providers is provided, which can include estimated time to arrival (for traveling to the provider location), estimated wait time, estimated cost, and/or other information associated with the healthcare providers. In some embodiments, the patient is administered a treatment based on a diagnosed or detected ophthalmic disease or condition. In some embodiments, the patient is administered a recommended treatment based on a diagnosed or detected ophthalmic or systemic disease or condition. In some embodiments, the systems, methods, and devices disclosed herein provide a recommendation for further testing. Further testing can include a medical exam such as a dilated eye exam or additional imaging such as OCT imaging for detecting diabetic retinopathy. Tonometry can be used to measure pressure within the eye to detect glaucoma, and ophthalmoscopy during a medical exam can detect optic nerve damage indicative of glaucoma. Other glaucoma tests include perimetry, gonioscopy, and pachymetry. Macular degeneration can be detected using further testing such as an eye exam, which can include an Amsler grid test, angiography (e.g., using fluorescein or indocyanine), or OCT imaging.

Various algorithms can be used to generate models that generate a prediction based on the image analysis. In some instances, machine learning methods are applied to the generation of such models (e.g. trained classifier). In some embodiments, the model is generated by providing a machine learning algorithm with training data in which the expected output is known in advance.

In some embodiments, the systems, methods, and software disclosed herein generate a report comprising the results of the analysis of an ophthalmic image. The report can include the image classification, one or more performance metrics of the classification (e.g., accuracy), referral to a healthcare provider for treatment and/or confirmation of the classification, general information for the disease, disorder, or condition corresponding to the image classification, treatment information, recommendations, or other relevant information. In some embodiments, the report is provided to a clinician, the subject of the report, a third party, or a combination thereof. In some embodiments, the medical insight is simplified into layman's terms for a non-clinician or medical practitioner such as the subject or a third party (e.g., parent of the subject). In some embodiments, the report comprises an occlusion image (e.g., image showing areas of greatest importance) used in the diagnosis or prediction.

In some embodiments, the systems, devices, and methods described herein generate one or more recommendations such as treatment and/or healthcare options for a subject. In some embodiments, the systems, devices, and methods herein comprise a software module providing one or more recommendations to a user. In some embodiments, the treatment and/or healthcare option are specific to the diagnosed disease or condition. For example, a recommendation can suggest a nearby hospital, doctor, or clinic with the requisite facilities or resources for treating the disease or disorder In some embodiments, a classifier or trained machine learning algorithm of the present disclosure comprises a feature space. In some cases, the classifier comprises two or more feature spaces. The two or more feature spaces may be distinct from one another. In some embodiments, a feature space comprises information such as pixel data from an image. When training the machine learning algorithm, training data such as image data is input into the algorithm which processes the input features to generate a model. In some embodiments, the machine learning algorithm is provided with training data that includes the classification (e.g. diagnostic or test result), thus enabling the algorithm to train by comparing its output with the actual output to modify and improve the model. This is often referred to as supervised learning. Alternatively, in some embodiments, the machine learning algorithm can be provided with non-domain data, which leaves the algorithm to identify hidden structure amongst the cases (referred to as unsupervised learning). Sometimes, unsupervised learning is useful for identifying the features that are most useful for classifying raw data into separate cohorts.

In some embodiments, one or more sets of training data are used to train a machine learning algorithm. Although exemplar embodiments of the present disclosure include machine learning algorithms that use convolutional neural networks, various types of algorithms are contemplated. In some embodiments, the algorithm utilizes a predictive model such as a neural network, a decision tree, a support vector machine, or other applicable model. In some embodiments, the machine learning algorithm is selected from the group consisting of a supervised, semi-supervised and unsupervised learning, such as, for example, a support vector machine (SVM), a Naïve Bayes classification, a random forest, an artificial neural network, a decision tree, a K-means, learning vector quantization (LVQ), self-organizing map (SOM), graphical model, regression algorithm (e.g., linear, logistic, multivariate), association rule learning, deep learning, dimensionality reduction and ensemble selection algorithms. In some embodiments, the machine learning algorithm is selected from the group consisting of: a support vector machine (SVM), a Naïve Bayes classification, a random forest, and an artificial neural network. Machine learning techniques include bagging procedures, boosting procedures, random forest algorithms, and combinations thereof. Illustrative algorithms for analyzing the data include but are not limited to methods that handle large numbers of variables directly such as statistical methods and methods based on machine learning techniques. Statistical methods include penalized logistic regression, prediction analysis of microarrays (PAM), methods based on shrunken centroids, support vector machine analysis, and regularized linear discriminant analysis.

Diagnostic Platforms, Systems, Devices, and Media

Provided herein, in certain aspects, are platforms, systems, devices, and media for analyzing medical data according to any of the methods of the present disclosure. In some embodiments, the systems and electronic devices are integrated with a program including instructions executable by a processor to carry out analysis of medical data. In some embodiments, the analysis comprises processing at least one medical image with a classifier such as a neural network, optionally trained on non-domain medical images using transfer learning. In some embodiments, the analysis is performed locally on the device utilizing local software integrated into the device. In some embodiments, the analysis is performed remotely on a remote system or server. In some embodiments, the analysis is performed remotely on the cloud after the image is uploaded by the system or device over a network. In some embodiments, the system or device is an existing system or device adapted to interface with a web application operating on the network or cloud for uploading and analyzing image data such as ophthalmic images. In some embodiments, the system or device provides for portable image storage such as on a USB drive or other portable hard drive. Portable storage enables the images to be transferred to a device capable of performing analysis on the images and/or which has network connectivity for uploading the images for remote analysis on the cloud.

Cloud-Based Diagnosis

Provided herein, in certain embodiments, are systems, devices, and methods for providing a web application or portal for remote data analysis or diagnosis (e.g., "cloud" diagnosis). In some embodiments, the application allows a user to load a trained model and predicts the diagnosis of any user-provided image. In some embodiments, the application provides a breakdown of the diagnosis such as generated using softmax probabilities. In some embodiments, the application allows a user to test the algorithm and upload smartphone captures of fundus images and yields comparable accuracy to clinician diagnoses. In some embodiments, the application is in communication with a diagnostic or imaging device as described herein. For example, a diagnostic or imaging device used at the point of care such as at a hospital or outside of the clinic setting (e.g. using a portable diagnostic or imaging device at home) can be used to obtain an image of a subject that is then uploaded over a network such as the Internet for remote diagnosis using the application. The diagnosis can then be provided to the user who uploaded the image and/or the subject from whom the image was obtained. In some embodiments, the diagnosis and/or any additional information (e.g. statistical breakdown, instructions, treatment recommendations, etc) is provided to the user and/or subject using e-mail, text messaging, a web portal, regular mail, or other available communication method. In some embodiments, the diagnosis and/or additional information is provided through a secure HIPAA-compliant application or portal (e.g. requiring secured and encrypted login). In some embodiments, the user and/or subject is sent a non-identifying message containing a link and/or information allowing the user or subject to retrieve the diagnosis and/or additional information from a secure storage location such as through a HIPAA-compliant portal.

Furthermore, the disclosed network represents a generalized platform which can potentially apply to a very wide range of medical imaging techniques (e.g. MRI, CT, etc.) to make a clinical diagnostic decision. This could facilitate screening programs and create more efficient referral systems, particularly in remote or low-resource areas, leading to a broad clinical and public health impact.

In some aspects, disclosed herein is a computer-implemented system configured to carry out cloud-based analysis of medical data such as ophthalmic images. In some embodiments, the system comprises one or more servers operatively coupled to a network. In some embodiments, the system is configured to provide a web portal, including a browser-based web portal, web-based application, or web-based application programming interface (API) accessible by end users on the network. In some embodiments, the web portal comprises an interface for receiving user instructions and/or medical data uploads. In some embodiments, the system receives at least one ophthalmic image from an end user or electronic device of an end user. In some embodiments, the ophthalmic image is captured by the electronic device of the end user at the point of care and uploaded to the system on the cloud for analysis. In some embodiments, the web portal is secured by encrypted password protected login. In some embodiments, the system receives uploaded instructions and/or medical data and performs analysis of the medical data using any of the diagnostic methods described herein. In some embodiments, the system generates output from the analysis of the medical data. In some embodiments, the system provides the output of the analysis to the end user on the network. In some embodiments, the system sends the output to an electronic device of the end user such as a computer, smartphone, tablet or other digital processing device configured for network communications.

Hardware/Software Integration

Disclosed herein, in some aspects, are electronic devices comprising software configured for performing the machine learning algorithms described herein. In some embodiments, the electronic device comprises an imaging component for capturing an image of a subject, a user interface for communicating with and/or receiving instructions from a user or subject, a memory, at least one processor, and non-transitory computer readable media providing instructions executable by the at least one processor for performing analysis of the captured image. In some embodiments, the electronic device comprises a network component for communicating with a network or cloud. The network component is configured to communicate over a network using wired or wireless technology. In some embodiments, the network component communicates over a network using Wi-Fi, Bluetooth, 2G, 3G, 4G, 4G LTE, 5G, WiMAX, WiMAN, or other radiofrequency communication standards and protocols.

In some embodiments, the system or electronic device captures a plurality of images for analysis. In some embodiments, the plurality of images are merged and/or analyzed collectively. In some embodiments, the electronic device is not configured to carry out analysis of the captured image locally, instead uploading the captured image to a network for cloud-based or remote analysis. In some embodiments, the electronic device comprises a web portal application that interfaces with the network or cloud for remote analysis and does not carry out any analysis locally. An advantage of this configuration is that image data is not stored locally and thus less vulnerable to being hacked or lost. Alternatively or in combination, the electronic device is configured to carry out analysis of the captured image locally. An advantage of this configuration is the ability to perform analysis in locations lacking network access or coverage (e.g. in certain remote locations lacking internet coverage). In some embodiments, the electronic device is configured to carry out analysis of the captured image locally when network access is not available as a backup function such as in case of an internet outage or temporary network failure. In some embodiments, the image data is uploaded for storage on the cloud regardless of where the analysis is carried out. For example, in certain instances, the image data is temporarily stored on the electronic device for analysis, and subsequently uploaded on the cloud and/or deleted from the electronic device's local memory.

In some embodiments, the system comprises the electronic device and cloud-based server(s) carrying out the analysis and/or storing the image data. In some embodiments, the system comprises the electronic device and an imaging component physically separate from the electronic device. As an example, the system comprises an electronic device that is a desktop computer coupled to or otherwise in communication with an imaging component (e.g. a retinal camera). In some embodiments, the system allows for an image to be captured using the imaging component, and the analysis to be performed by the electronic device, or alternatively, by the cloud following upload of the image. In some embodiments, the system comprises the electronic device for analyzing and/or uploading an image, an imaging component for capturing an image and configured to send the image or image data to the electronic device, and a cloud-based server for receiving an uploaded image and storing and/or analyzing the image, and generating a result to be provided to a user via the electronic device or other methods such as by messaging, email, or a phone call. In some embodiments, the system or device comprises a plurality of imaging components. In some embodiments, the plurality of imaging components is configured to capture multiple types of images. In some embodiments, analysis of the multiple types of images is carried out by different classifiers trained on the different image types to provide more than one diagnosis or result. Alternatively, in some embodiments, the more than one diagnosis or result is consolidated or combined into a single result metric (e.g. an average of the predictions for a particular disorder).

In some embodiments, the electronic device comprises a display for providing the results of the analysis such as a diagnosis or prediction (of the presence and/or progression of a disease or disorder), a treatment recommendation, treatment options, healthcare provider information (e.g. nearby providers that can provide the recommended treatment and/or confirm the diagnosis), or a combination thereof. In some embodiments, the diagnosis or prediction is generated from analysis of the captured image in comparison to previously captured image(s) for the same user to determine the progression of a disease or disorder. In some embodiments, captured images are time-stamped. In some embodiments, captured images are stored as data, which optionally includes meta-data such as a timestamp, location, user info, or other information associated with the images). In some embodiments, the image data is screened for quality. In some embodiments, the image is screened for suitability for analysis. In some embodiments, an image failing the screen is discarded or otherwise rejected from further analysis. In some embodiments, the electronic device prompts a user to take one or more additional images.

In some embodiments, the electronic device comprises a portal providing one or more tools for a user to input information such as name, address, email, phone number, and/or other identifying information. In some embodiments, the portal comprises an interface for obtaining or entering medical data. In some embodiments, the portal is configured to receive medical data for use in the prediction or diagnosis from device through a network (e.g. receives medical data provided by a user smartphone through the interne via a mobile app or web portal).

In some embodiments, the portal is configured to provide a health assessment through the electronic device. In some embodiments, the health assessment comprises a diagnosis of an ophthalmic disease or condition. In some embodiments, the ophthalmic disease or condition is a predicted visual outcome following a medical procedure. In some embodiments, the predicted visual outcome is myopic maculopathy following a medical procedure that is cataract surgery.

In some embodiments, the portal provides the user with the option to receive the results of the analysis by email, messaging (e.g. SMS, text message), physical printout (e.g. a printed report), social media, by phone (e.g. an automated phone message or a consultation by a healthcare provider or adviser), or a combination thereof. In some embodiments, the captured image(s) is provided to the user. For example, an image can be shown with graphical emphasis (e.g. highlighting, boundaries drawn around the areas, zoomed in view, etc) on the areas that are most important to the diagnosis as identified by the occlusion test, which can help promote understanding and trust in the diagnostic method. In some embodiments, the portal is displayed on a digital screen of the electronic device. In some embodiments, the electronic device comprises an analog interface. In some embodiments, the electronic device comprises a digital interface such as a touchscreen. In various embodiments, existing systems and devices are capable of being adapted to carry out the methods disclosed herein or are capable of interfacing with web applications for performing remote analysis of ophthalmic images. Examples of such systems and electronic include non-mydriatic retinal cameras such as the TRC-NW400 retinal camera, CR-2 retinal camera, S40ptik Cobra fundus camera, and Volk Pictor Plus Portable Retinal Camera.

In some embodiments, the electronic device has a hardware configuration adapted for capturing images of a subject for analysis according to the methods described herein. In some embodiments, the electronic device comprises a specialized imaging component such as a camera operatively coupled to an ophthalmoscope. In some embodiments, the camera and ophthalmoscope are configured as a single integrated unit. In some embodiments, the camera, ophthalmoscope, and electronic device are configured as a single integrated unit such as a portable diagnostic device. In some embodiments, the imaging component is a digital ophthalmoscope. In some embodiments, the imaging component is configured to capture images and/or video (including stills from the video). In some embodiments, the captured images are high definition photos. As used herein, high definition can refer to photos having 1920×1080 or more pixels. In some embodiments, the captured images are fundus photographs or other images as described throughout the present disclosure.

Kiosk

In some embodiments, the system or electronic device is a kiosk or a component of a kiosk. In some embodiments, the kiosk comprises an enclosure storing internal components such as the imaging component, processor, memory, storage, network component, and other hardware. In some embodiments, the kiosk comprises a seat for seating a user in front of the imaging component. In some embodiments, the kiosk comprises a positioning component for positioning the head of the user in front of the imaging component to capture an image. In some embodiments, the positioning component is configured to reduce head tilt. Because the eye is a 3-dimensional structure, the direction of the visual axis and ocular cyclotorsion can distort images that are taken of the eye and its internal structures. Thus, head tilt can result in ocular cyclotorsion and potentially negatively impact the quality and consistency of captured ophthalmic images. Accordingly, in some embodiments, the systems and devices disclosed herein such as a kiosk comprise a head positioner that reduces and/or manages head tilt to reduce the impact of ocular cyclotorsion on image quality or analysis. In some embodiments, the head positioner comprises a chin rest and a forehead rest configured to position the head of the user at a neutral or close to neutral position that minimizes forward or backward head tilt. In some embodiments, the head positioner comprises lateral rests or supports for minimizing or reducing lateral head tilt. In some embodiments, the head positioner is user adjustable. In some embodiments, the systems and devices disclosed herein are configured to capture and display a video feed or camera image of the user's head to aid in positioning the head to minimize head tilt.

In some embodiments, the kiosk comprises an interface for obtaining or entering medical data. In some embodiments, the kiosk is configured to receive medical data for use in the prediction or diagnosis from another device such as through a network (e.g. receives medical data provided by a user smartphone through the internet via a mobile app or web portal).

In some embodiments, the kiosk is configured to provide more than one health assessment. In some embodiments, the health assessment comprises a diagnosis of an ophthalmic or systemic disease or condition. In some embodiments, the kiosk comprises one or more tools for measuring a user's weight, pulse, blood pressure (systolic and diastolic), body mass index (BMI), hydration, body fat content, or a combination thereof. In some embodiments, the kiosk comprises a seat that is configured to act as a scale for measuring the weight of a seated user. In some embodiments, the seat and a floor of the kiosk operate together as a scale. In some embodiments, the kiosk comprises a floor that acts as a scale for measuring the user's weight. In some embodiments, the kiosk comprises a footrest such that the seat and the footrest act as a scale for measuring the user's bodyweight. In some embodiments, the kiosk comprises a blood pressure cuff configured to measure blood pressure and pulse. In some embodiments, the kiosk comprises a body fat analyzer. In some embodiments, the body fat analyzer is an impedance meter configured to measure a body's electrical impedance. In some embodiments, the body fat analyzer is configured to measure body composition, which can include the estimated amounts of fat, bone, water, muscle, or a combination thereof. In some embodiments, the kiosk is configured to capture an ophthalmic image from a user. Alternatively or in combination, the kiosk is configured to measure the user's weight, pulse, blood pressure, hydration, body fat content, or a combination thereof.

Portable Diagnostic Device

In some embodiments, the electronic device is a portable device configured to be handheld or otherwise capable of being transported by an individual. In some embodiments, the portable device comprises an interface for obtaining or entering medical data. In some embodiments, the portable device is configured to receive medical data for use in the prediction or diagnosis from another device such as through a network (e.g. receives medical data provided by a user smartphone through the interne via a mobile app or web portal). In some embodiments, the portable device comprises a camera for capturing medical images. In some embodiments, the portable device comprises a specialized camera for capturing ophthalmic images. In some embodiments, the specialized camera is a retinal scanner. In some embodiments, the retinal scanner is a non-mydriatic fundus camera. In some embodiments, the retinal scanner performs digital retinal imaging. In some embodiments, the retinal scanner is any one of the imaging devices described throughout the present disclosure. In some embodiments, the portable device comprises a digital processing device for processing the captured image and/or generating a diagnosis or diagnostic prediction. In some embodiments, the portable device is configured to upload one or more captured images onto a network for remote prediction. In some embodiments, the portable device comprises a digital processing device configured to analyze the captured image to generate a prediction. In some embodiments, the portable device is configured to receive updates to the software of the digital processing device (e.g. updating the CNN). In some embodiments, the portable device is configured to analyze the captured image locally when remote prediction is unavailable (e.g. due to lack of network access) or upload the captured image when remote prediction is available.

In some embodiments, the portable device is configured to capture an ophthalmic image in conjunction with a user electronic device such as a smartphone, tablet, laptop, or computer. In some embodiments, the portable device is configured to communicate with the user electronic device through wired and/or wireless technologies. For example, the portable device can be physically connected to the user electronic device through a cable such as a USB, microUSB, or Lightning cable. In some embodiments, wired connections allow the portable device to receive power and/or charge from the user electronic device. As an example, a specialized miniature camera for imaging a user's retina and an optional flash can be powered by a user's smartphone through a USB connection. In some embodiments, the portable device communicates wirelessly with the user electronic device. In some embodiments, the portable device is configured to send a captured image to the user electronic device via a cable and/or wirelessly. In some embodiments, the user electronic device comprises a program such as a mobile application that interfaces with a web application and uploads the captured image to the web application for analysis remotely on the network or cloud.

In some embodiments, the portable device comprises an ophthalmoscope and is configured to align the ophthalmoscope with a camera on a user electronic device to allow a fundus image of a subject's eye to be captured by the camera with the aid of the ophthalmoscope. As a non-limiting example, the portable device is configured to align the ophthalmoscope with a smartphone camera (e.g. an Android phone or iPhone). In some embodiments, the portable device is configured to align the ophthalmoscope with a front-facing camera (e.g. facing the user and/or on the same side as a touchscreen), a rear-facing camera (e.g. facing away from the user), or both. In some embodiments, the portable device is configured to allow user adjustment of the alignment between the ophthalmoscope and the camera of the user electronic device. In some embodiments, the portable device comprises an adaptor shaped to attach to or clip onto a user electronic device. In some embodiments, the adaptor is configured to snugly fit around the outside contour of the user electronic device. In some embodiments, the adaptor comprises a smartphone case. In some embodiments, the smartphone case adaptor is shaped for a specific phone model so as to position the ophthalmoscope in alignment with the phone's camera (front and/or rear). In some embodiments, the adaptor comprises an adjustable strap that can wrap around the user electronic device (e.g. a Velcro strap that can be tightened around the phone). In some embodiments, the ophthalmoscope is coupled to the adaptor. In some embodiments, the ophthalmoscope is detachably coupled to the adaptor. In some embodiments, the ophthalmoscope is movable relative to the adaptor to enable user adjustment of the positioning of the ophthalmoscope to the camera of the user electronic device after the adaptor has been properly mounted to the electronic device. For example, the ophthalmoscope can be coupled to the adaptor via a flexible attachment that can be adjusted to move the ophthalmoscope relative to the adaptor, and thus to the camera of the electronic device.

In some embodiments, the user electronic device is configured to capture an ophthalmic image using its camera in combination with the ophthalmoscope. In some embodiments, the user electronic device is configured to capture a plurality of ophthalmic images. In some embodiments, the plurality of ophthalmic images is screened in which analysis is carried out on out one or more images passing the quality screening. In some embodiments, the user electronic device is configured to capture video. In some embodiments, the captured video is screened to identify one or more screenshots of the video, and those screenshot(s) passing the quality control screen are subsequently analyzed to provide a result such as a diagnosis and/or treatment recommendation. In some embodiments, the ophthalmoscope interfaces with both the camera and a flash of the user electronic device such that the flash passes through a filter of the ophthalmoscope for modulating the intensity of the flash. In some embodiments, the ophthalmoscope comprises a semi-transparent area covering the flash to reduce the intensity of the light flash. In some embodiments, the semi-transparent area is adjustable (e.g. the semi-transparent area is a filter that can be removed and replaced with another filter from a set of filters of varying opacity).

In some embodiments, the user electronic device is configured to provide instructions or warnings to a user while capturing the ophthalmic image or video. An advantage of using video is this approach allows the ophthalmoscope to be repositioned with respect to the eye or pupil to capture different areas of the retina and/or fundus over time. For example, some forms of traditional imaging require pupil dilation since undilated pupils will obstruct a complete view of the ocular structures. However, in the case of a patient or non-healthcare provider attempting to capture the ophthalmic image outside of the clinic environment, access to dilating eye drops may not be available. Accordingly, in some embodiments, ophthalmic data is obtained through a video feed, wherein screenshots from the video feed are stitched together to generate a composite image of the areas of the eye that are important for accurate analysis according to the various methods described herein. As an example, the user electronic device is a smartphone comprising a mobile application that visualizes the ophthalmoscope-enhanced camera feed of a subject's eye on its display screen. In some embodiments, the mobile application actively monitors the camera feed and provides instructions for properly capturing an ophthalmic image or video. In some cases, the instructions include steps for carrying out the image capture protocol. In some instances, a warning is provided indicating the camera is not properly aligned with the ophthalmoscope or the pupil, the feed is blurry, the camera/user device is shaking, the feed is being obstructed, or other complications interfering with image capture. In some embodiments, the instructions and/or warnings are provided visually on the screen of the user electronic device. In some embodiments, the instructions and/or warnings are provided by audio (e.g. the instructions/warnings are vocalized through an audio speaker of the user electronic device).

In some embodiments, the portable device is configured to be used by a user to capture an ophthalmic image of an eye of a subject who is not the user. In some embodiments, the portable device is configured to be used by a user to capture an ophthalmic image of the user's own eye. As an example, a smartphone configured to position an ophthalmoscope over a front-facing camera can provide instructions and/or warnings on its display screen enabling a user to self-position the ophthalmoscope to align with his eye (e.g. aligning the ophthalmoscope with his pupil). Alternatively, a smartphone configured to position an ophthalmoscope over a rear-facing camera can provide audio instructions and/or warnings. Non-limiting examples of instructions in no particular order include: 1) explaining the procedure to the user (e.g. the duration of the procedure, whether the user will be exposed to a bright light); 2) instructions to apply one or more mydriatic eye drops to dilate the pupils; 3) instructions on where to look (e.g. a distant object with the non-imaged eye); 4) how to align the ophthalmoscope with the user electronic device; 5) how to align the ophthalmoscope with the eye or pupil; 6) distance to hold the ophthalmoscope from the eye; and 7) instructions to hold still when the alignment is correct.

In some embodiments, the medical data comprises medical images such as ophthalmic images. In some embodiments, the ophthalmic images comprise retinal images. In some embodiments, the system or device comprises an imaging component for capturing an image of a subject. In some embodiments, the image is a retinal image. In some embodiments, the imaging component is configured for optical coherence tomography (OCT), color fundus photography of the retina (CFP), corneal topography, slit-lamp photography, fluorescein angiography, indocyanine green angiography, fundus auto-fluorescence, optic nerve head analysis, endothelial cell-layer imaging, or external imaging such as standard photography. In some embodiments, ophthalmic images are generated using specialized imaging equipment. In some embodiments, a digital retinal camera is used for color fundus photography and fluorescein angiography. In some embodiments, the imaging component is an optical coherence tomography, a scanning laser ophthalmoscope, photo slit-lamp micrography, corneal topography, an optic nerve head analyzer, a photographic camera, or a Rostock corneal module (RCM). In some embodiments, the imaging component is an automated camera for capturing a retinal image (e.g. an automated fundus camera).

Digital Processing Device

In some embodiments, the systems, devices, platforms, media, methods and applications described herein include a digital processing device, a processor, or use of the same. For example, in some embodiments, the digital processing device is part of a point-of-care device such as a medical diagnostic device integrating the diagnostic software described herein. In some embodiments, the medical diagnostic device is a consumer-facing portable medical diagnostic device configured for use outside of the clinical setting (e.g. consumer use at home). In some embodiments, the medical diagnostic device comprises diagnostic equipment such as imaging hardware (e.g. a camera) for capturing medical data (e.g. medical images). In some embodiments, the medical diagnostic device comprises a digital processing device configured to perform the diagnostic methods described herein such as disease detection or classification based on medical images. In further embodiments, the digital processing device includes one or more processors or hardware central processing units (CPU) that carry out the device's functions. In still further embodiments, the digital processing device further comprises an operating system configured to perform executable instructions. In some embodiments, the digital processing device is optionally connected a computer network. In further embodiments, the digital processing device is optionally connected to the Internet such that it accesses the World Wide Web. In still further embodiments, the digital processing device is optionally connected to a cloud computing infrastructure. In other embodiments, the digital processing device is optionally connected to an intranet. In other embodiments, the digital processing device is optionally connected to a data storage device. In accordance with the description herein, suitable digital processing devices include, by way of non-limiting examples, server computers, desktop computers, laptop computers, notebook computers, sub-notebook computers, netbook computers, netpad computers, set-top computers, handheld computers, Internet appliances, mobile smartphones, tablet computers, personal digital assistants, video game consoles, and vehicles. Those of skill in the art will recognize that many smartphones are suitable for use in the system described herein. Those of skill in the art will also recognize that select televisions, video players, and digital music players with optional computer network connectivity are suitable for use in the system described herein. Suitable tablet computers include those with booklet, slate, and convertible configurations, known to those of skill in the art.

In some embodiments, the digital processing device includes an operating system configured to perform executable instructions. The operating system is, for example, software, including programs and data, which manages the device's hardware and provides services for execution of applications. Those of skill in the art will recognize that suitable server operating systems include, by way of non-limiting examples, FreeBSD, OpenBSD, NetBSD®, Linux, Apple® Mac OS X Server®, Oracle® Solaris®, Windows Server®, and Novell® NetWare®. Those of skill in the art will recognize that suitable personal computer operating systems include, by way of non-limiting examples, Microsoft® Windows®, Apple® Mac OS X®, UNIX®, and UNIX-like operating systems such as GNU/Linux®. In some embodiments, the operating system is provided by cloud computing. Those of skill in the art will also recognize that suitable mobile smart phone operating systems include, by way of non-limiting examples, Nokia® Symbian® OS, Apple® iOS®, Research In Motion® BlackBerry OS®, Google® Android®, Microsoft® Windows Phone® OS, Microsoft® Windows Mobile® OS, Linux®, and Palm® WebOS®.

In some embodiments, the device includes a storage and/or memory device. The storage and/or memory device is one or more physical apparatuses used to store data or programs on a temporary or permanent basis. In some embodiments, the device is volatile memory and requires power to maintain stored information. In some embodiments, the device is non-volatile memory and retains stored information when the digital processing device is not powered. In further embodiments, the non-volatile memory comprises flash memory. In some embodiments, the non-volatile memory comprises dynamic random-access memory (DRAM). In some embodiments, the non-volatile memory comprises ferroelectric random access memory (FRAM). In some embodiments, the non-volatile memory comprises phase-change random access memory (PRAM). In some embodiments, the non-volatile memory comprises magnetoresistive random-access memory (MRAM). In other embodiments, the device is a storage device including, by way of non-limiting examples, CD-ROMs, DVDs, flash memory devices, magnetic disk drives, magnetic tapes drives, optical disk drives, and cloud computing based storage. In further embodiments, the storage and/or memory device is a combination of devices such as those disclosed herein.

In some embodiments, the digital processing device includes a display to send visual information to a subject. In some embodiments, the display is a cathode ray tube (CRT). In some embodiments, the display is a liquid crystal display (LCD). In further embodiments, the display is a thin film transistor liquid crystal display (TFT-LCD). In some embodiments, the display is an organic light emitting diode (OLED) display. In various further embodiments, on OLED display is a passive-matrix OLED (PMOLED) or active-matrix OLED (AMOLED) display. In some embodiments, the display is a plasma display. In some embodiments, the display is E-paper or E ink. In other embodiments, the display is a video projector. In still further embodiments, the display is a combination of devices such as those disclosed herein.

In some embodiments, the digital processing device includes an input device to receive information from a subject. In some embodiments, the input device is a keyboard. In some embodiments, the input device is a pointing device including, by way of non-limiting examples, a mouse, trackball, track pad, joystick, game controller, or stylus. In some embodiments, the input device is a touch screen or a multi-touch screen. In other embodiments, the input device is a microphone to capture voice or other sound input. In other embodiments, the input device is a video camera or other sensor to capture motion or visual input. In further embodiments, the input device is a Kinect, Leap Motion, or the like. In still further embodiments, the input device is a combination of devices such as those disclosed herein.

Figure 11:
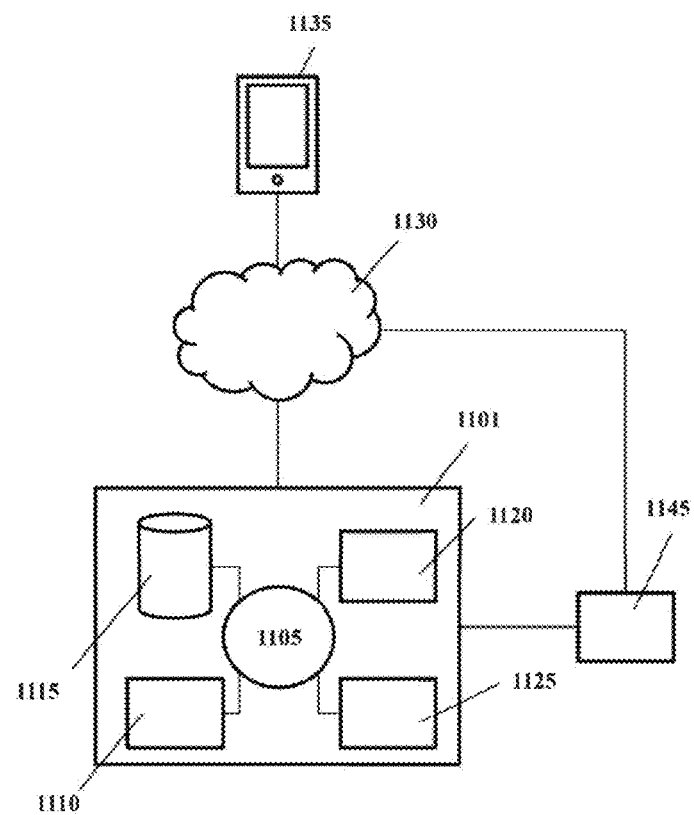
FIG. 11 schematically illustrates a computer control system or platform that is programmed or otherwise configured to implement methods provided herein, according to an embodiment.

FIG. 11 schematically illustrates a computer control system or platform that is programmed or otherwise configured to implement methods provided herein. In some embodiments, the system comprises a computer system 1101 that is programmed or otherwise configured to carry out executable instructions such as for carrying out image analysis. The computer system includes at least one CPU or processor 1105. The computer system includes at least one memory or memory location 1110 and/or at least one electronic storage unit 1115. In some embodiments, the computer system comprises a communication interface 1120 (e.g. network adaptor). In some embodiments, the computer system 1101 can be operatively coupled to a computer network ("network") 1130 with the aid of the communication interface 1120. In some embodiments, an end user device 1135 is used for uploading medical data such as ophthalmic images, general browsing of the database 1145, or performance of other tasks. In some embodiments, the database 1145 is one or more databases separate from the computer system 1101.

Non-Transitory Computer Readable Storage Medium

In some embodiments, the platforms, media, methods and applications described herein include one or more non-transitory computer readable storage media encoded with a program including instructions executable by the operating system of an optionally networked digital processing device. In further embodiments, a computer readable storage medium is a tangible component of a digital processing device. In still further embodiments, a computer readable storage medium is optionally removable from a digital processing device. In some embodiments, a computer readable storage medium includes, by way of non-limiting examples, CD-ROMs, DVDs, flash memory devices, solid state memory, magnetic disk drives, magnetic tape drives, optical disk drives, cloud computing systems and services, and the like. In some cases, the program and instructions are permanently, substantially permanently, semi-permanently, or non-transitorily encoded on the media.

Computer Program

In some embodiments, the platforms, media, methods and applications described herein include at least one computer program, or use of the same. A computer program includes a sequence of instructions, executable in the digital processing device's CPU, written to perform a specified task. Computer readable instructions may be implemented as program modules, such as functions, objects, Application Programming Interfaces (APIs), data structures, and the like, that perform particular tasks or implement particular abstract data types. In light of the disclosure provided herein, those of skill in the art will recognize that a computer program may be written in various versions of various languages.

The functionality of the computer readable instructions may be combined or distributed as desired in various environments. In some embodiments, a computer program comprises one sequence of instructions. In some embodiments, a computer program comprises a plurality of sequences of instructions. In some embodiments, a computer program is provided from one location. In other embodiments, a computer program is provided from a plurality of locations. In various embodiments, a computer program includes one or more software modules. In various embodiments, a computer program includes, in part or in whole, one or more web applications, one or more mobile applications, one or more standalone applications, one or more web browser plug-ins, extensions, add-ins, or add-ons, or combinations thereof.

Web Application

In some embodiments, a computer program includes a web application. In light of the disclosure provided herein, those of skill in the art will recognize that a web application, in various embodiments, utilizes one or more software frameworks and one or more database systems. In some embodiments, a web application is created upon a software framework such as Microsoft® .NET or Ruby on Rails (RoR). In some embodiments, a web application utilizes one or more database systems including, by way of non-limiting examples, relational, non-relational, object oriented, associative, and XML database systems. In further embodiments, suitable relational database systems include, by way of non-limiting examples, Microsoft® SQL Server, mySQL™, and Oracle®. Those of skill in the art will also recognize that a web application, in various embodiments, is written in one or more versions of one or more languages. A web application may be written in one or more markup languages, presentation definition languages, client-side scripting languages, server-side coding languages, database query languages, or combinations thereof. In some embodiments, a web application is written to some extent in a markup language such as Hypertext Markup Language (HTML), Extensible Hypertext Markup Language (XHTML), or eXtensible Markup Language (XML). In some embodiments, a web application is written to some extent in a presentation definition language such as Cascading Style Sheets (CSS). In some embodiments, a web application is written to some extent in a client-side scripting language such as Asynchronous Javascript and XML (AJAX), Flash® Actionscript, Javascript, or Silverlight®. In some embodiments, a web application is written to some extent in a server-side coding language such as Active Server Pages (ASP), ColdFusion®, Perl, Java™, JavaServer Pages (JSP), Hypertext Preprocessor (PHP), Python™, Ruby, Tcl, Smalltalk, WebDNA®, or Groovy. In some embodiments, a web application is written to some extent in a database query language such as Structured Query Language (SQL). In some embodiments, a web application integrates enterprise server products such as IBM® Lotus Domino®. In some embodiments, a web application includes a media player element. In various further embodiments, a media player element utilizes one or more of many suitable multimedia technologies including, by way of non-limiting examples, Adobe® Flash®, HTML 5, Apple® QuickTime®, Microsoft® Silverlight®, Java™, and Unity®.

Mobile Application

In some embodiments, a computer program includes a mobile application provided to a mobile digital processing device such as a smartphone. In some embodiments, the mobile application is provided to a mobile digital processing device at the time it is manufactured. In other embodiments, the mobile application is provided to a mobile digital processing device via the computer network described herein.

In view of the disclosure provided herein, a mobile application is created by techniques known to those of skill in the art using hardware, languages, and development environments known to the art. Those of skill in the art will recognize that mobile applications are written in several languages. Suitable programming languages include, by way of non-limiting examples, C, C++, C#, Objective-C, Java™, Javascript, Pascal, Object Pascal, Python™, Ruby, VB.NET, WML, and XHTML/HTML with or without CSS, or combinations thereof.

Suitable mobile application development environments are available from several sources. Commercially available development environments include, by way of non-limiting examples, AirplaySDK, alcheMo, Appcelerator®, Celsius, Bedrock, Flash Lite, .NET Compact Framework, Rhomobile, and WorkLight Mobile Platform. Other development environments are available without cost including, by way of non-limiting examples, Lazarus, MobiFlex, MoSync, and Phonegap. Also, mobile device manufacturers distribute software developer kits including, by way of non-limiting examples, iPhone and iPad (iOS) SDK, Android™ SDK, BlackBerry® SDK, BREW SDK, Palm® OS SDK, Symbian SDK, webOS SDK, and Windows® Mobile SDK.

Those of skill in the art will recognize that several commercial forums are available for distribution of mobile applications including, by way of non-limiting examples, Apple® App Store, Android™ Market, BlackBerry® App World, App Store for Palm devices, App Catalog for webOS, Windows® Marketplace for Mobile, Ovi Store for Nokia® devices, Samsung® Apps, and Nintendo® DSi Shop.

Standalone Application

In some embodiments, a computer program includes a standalone application, which is a program that is run as an independent computer process, not an add-on to an existing process, e.g. not a plug-in. Those of skill in the art will recognize that standalone applications are often compiled. A compiler is a computer program(s) that transforms source code written in a programming language into binary object code such as assembly language or machine code. Suitable compiled programming languages include, by way of non-limiting examples, C, C++, Objective-C, COBOL, Delphi, Eiffel, Java™, Lisp, Python™, Visual Basic, and VB .NET, or combinations thereof. Compilation is often performed, at least in part, to create an executable program. In some embodiments, a computer program includes one or more executable complied applications.

Software Modules

In some embodiments, the platforms, media, methods and applications described herein include software, server, and/or database modules, or use of the same. In view of the disclosure provided herein, software modules are created by techniques known to those of skill in the art using machines, software, and languages known to the art. The software modules disclosed herein are implemented in a multitude of ways. In various embodiments, a software module comprises a file, a section of code, a programming object, a programming structure, or combinations thereof. In further various embodiments, a software module comprises a plurality of files, a plurality of sections of code, a plurality of programming objects, a plurality of programming structures, or combinations thereof. In various embodiments, the one or more software modules comprise, by way of non-limiting examples, a web application, a mobile application, and a standalone application. In some embodiments, software modules are in one computer program or application. In other embodiments, software modules are in more than one computer program or application. In some embodiments, software modules are hosted on one machine. In other embodiments, software modules are hosted on more than one machine. In further embodiments, software modules are hosted on cloud computing platforms. In some embodiments, software modules are hosted on one or more machines in one location. In other embodiments, software modules are hosted on one or more machines in more than one location.

Databases

In some embodiments, the platforms, systems, media, and methods disclosed herein include one or more databases, or use of the same. In view of the disclosure provided herein, those of skill in the art will recognize that many databases are suitable for storage and retrieval of barcode, route, parcel, subject, or network information. In various embodiments, suitable databases include, by way of non-limiting examples, relational databases, non-relational databases, object oriented databases, object databases, entity-relationship model databases, associative databases, and XML databases. In some embodiments, a database is internet-based. In further embodiments, a database is web-based. In still further embodiments, a database is cloud computing-based. In other embodiments, a database is based on one or more local computer storage devices.

EXAMPLES

Example 1

Detection of Ophthalmic and Systemic Diseases

Fundus images were first de-identified to remove any patient related information. The grading process then implemented a two-tier system divided into phase I and phase II graders. Phase I encompassed less experienced graders consisting of medical students, college students, and college graduates, with a background in medicine or other biologically related fields. Phase I graders were required to undergo extensive training from ophthalmologists before obtaining and diagnosing assigned folders of 500 fundus images. Phase II graders consisted of general ophthalmologists and retina specialists who individually reviewed each image classified by phase I graders to ensure the correct diagnostic classification. To improve the consistency among phase II graders, a subset of classified images were further reviewed by senior ophthalmologists. After having reached an established consensus among grading, images were handed to the artificial intelligence team to undergo a final stage of data-preprocessing. To ensure that the dataset did not include duplicated images, all training sets were run through an algorithm that removes images with identical pixel binaries. Upon removal, the final dataset was then fed through our deep learning algorithm for image-based classification.

All images used in Asian glaucoma validation were obtained from 633 patients whose clinical records contained visual fields presenting with glaucoma.

Disease Criteria

One embodiment of disease criteria will now be described. Normal images were classified as retinas with no apparent abnormal features. These images include optic discs presenting with sharp margins and a cup-to-disc ratio of approximately 0.35; possible striated sheen from healthy retinal nerve fiber layer (NFL); no lesions; no apparent sub-retinal disruptions; no pigmentary changes, tumors, scars, or molds; and normal vasculature. An exception was given to images with less than a handful of small drusens that are often hallmarks of normal age progression. Respectively, medium- and large-sized drusen can often be early indications of age-related macular degeneration (AMD) and therefore excluded. To make a clear distinction between normal retinas and retinas with AMD, only advanced or late stage AMD with apparent macular damage from either dry AMD (geographic atrophy) or wet AMD such as choroidal neovascularization (CNV) were included in our definition of AMD. Diabetic retinopathy (DR) were separated into groups of severity and classified according to the International Clinical Diabetic Retinopathy Disease Severity Scale. In the multiclass comparison, moderate to proliferative DR were used in training and validation. Patients with hemoglobin A1C levels XX but with no apparent signs of retinopathy were considered as diabetic patients without retinopathy and were therefore defined as NDR for "No Diabetic Retinopathy." Glaucoma was defined as either having one or more of the following features: 1) concentric expansion with an optic cup-to-disc ratio greater than or equal to 0.5, 2) narrowing of the disk at either superior or inferior rim with localized nerve fiber layer defect (NFLD). Visual fields were used as an additional diagnostic tool to confirm the presence of glaucoma. These visual field defects include but are not limited to, nasal step, temporal wedge, superior arcuate with peripheral breakthrough and early inferior defect, tunnel vision defect with crescent sparing, and end-stage complete field loss. High myopia was defined by refraction of less than −6.00 diopters and the presence of one or more of the following findings: peripapillary chorioretinal atrophy, lacquer cracks, posterior staphyloma, and/or extensive myopia retinal degeneration. Retinal vein occlusion (RVO) included both non-ischemic or ischemic CRVO and major/macular BRVO. For the multiclass comparison, patients with normal retinas and low severity of cataracts were also included in training.

An alternative embodiment of disease criteria will now be described. Normal retinal images were defined as those with no clinically abnormal features and from individuals with no known ocular disease and hemoglobin A1C levels<6.0%. The image exclusion criteria based on optic nerve appearance were disk edema, whole or segmental disc pallor, or tilted disk. The image exclusion criteria based on retinal features included retinal nerve fiber layer (RNFL) defects, anomalous pigmentation, tumors, scars, folds, medium and large drusen, and abnormalities of retinal vessels (such as e.g. microaneurysms,focal and generalized arteriolar narrowing, and arteriovenous nicking, hemorrhages, new vessels, cotton wool spots, hard exudates). An exception was given to include images with less than five small drusen which can be the hallmark of normal aging. For images of AMD, in order to create a clear distinction between normal and disease, only advanced AMD with macular damage from either dry AMD (geographic atrophy) or wet AMD (choroidal neovascularization, CNV) were included. For binary comparison between active and inactive CNV, active CNV was defined by the presence of any subretinal hemorrhage, fluid or exudation. DR images were classified into severity groups according to Early Treatment of Diabetic Retinopathy Study (ETDRS) criteria. The diagnoses of diabetic macular edema (DME) were based on the presence of one or more of the following features on optical coherence tomography (OCT): (1) retinal thickening within 500 micrometers of the macular center, (2) hard exudates within 500 micrometers of the macular center with adjacent retinal thickening, (3) one or more disc diameters of retinal thickening, any part of which is within one disc diameter of the macular center. In the multiclass comparison, moderate to proliferative DR were used in training and validation. Patients with hemoglobin A1C levels>6.5% but no apparent signs of DR were considered as diabetic patients without retinopathy or NODR for "No Diabetic Retinopathy". Glaucoma was defined as having two or more of the following features: (1) vertical optic cup-to-disc ratio greater than or equal to 0.8, (2) superior or inferior disc notch or rim thinning, (3) RNFL defect radiating from the optic nerve head. Standard automated perimetry with the Humphrey Field Analyzer was used as an additional diagnostic tool. The perimetric criteria for glaucoma were pattern standard deviation (PSD)≥5% of normal, or glaucoma hemifield test and mean defect (MD) outside of normal limits on a Humphry visual field machine. High myopia was defined by the presence of one or more of the following: myopia degeneration, diffuse chorioretinal atrophy, patchy chorioretinal atrophy, lacquer cracks, posterior staphyloma, and myopic retinal degeneration. Retinal vein occlusion (RVO) included both non-ischemic and ischemic, central and branch vein occlusions.

Transfer Learning Methods

An Inception V3 architecture pretrained on the ImageNet dataset was then retrained using the PyTorch framework. Retraining consisted of initializing the convolutional layers with loaded pretrained weights along with a newly initialized final, softmax layer and training this model to recognize our selected classes. In this study, the convolutional layers were initially frozen and used as fixed feature extractors until training converged. Then the convolutional layers were unfrozen and fine-tuned for several more epochs. The training was conducted on an Ubuntu 18.04 server with an Intel Xeon CPU, using three NVIDIA GTX 1080 8Gb GPU for training and testing, with 128Gb available in RAM memory. Training of layers was performed by stochastic gradient descent in batches of 32 images for 25 epochs with a learning rate of 10-4. Holdout method testing was performed after every step using a test partition containing images from patients independent of the patients represented in the training partition by passing each image through the network without performing gradient descent and backpropagation, and the best performing model was kept for analysis.

Multiclass and Binary Classifications

Training and testing sets were divided as follows: the disease category with the lowest number of training images was split into a 20:80 ratio. This number of testing images was then used to define the image count of every other category.

Vessel Segmentation

The neural network architecture used to achieve vessel segmentation was derived from the U-net architecture. The loss function was the cross-entropy and the stochastic gradient descent was employed for optimization. The activation function after each convolutional layer was the Rectifier Linear Unit (ReLU), and a dropout of 0.2 was used between two consecutive convolutional layers. Training was performed for 100 epochs, with a batch size of 32 patches. Using a GeForce GTX 1080 GPU the training lasted for about 12 hours.

Before training, the training datasets were pre-processed by sequentially performing gray-scale conversion, contrast-limited adaptive histogram equalization (CLAHE), and, mean subtraction with standard deviation division.

The training of the neural network was performed on patches of the preprocessed full images. Each patch, of dimension 48×48, was obtained by randomly selecting its center inside the full image. In addition, the patches partially or completely outside the Field Of View (FOV) were selected, so that the neural network could learn how to discriminate the FOV border from blood vessels.

A set of 190,000 patches was obtained by randomly extracting 9,500 patches in each of the 20 DRIVE training images. The first 80% of the dataset was used for training, while the last 20% was used for validation.

During testing and inference, only the pixels belonging to the FOV were considered. The FOV was identified with the masks included in the DRIVE database. In order to improve the performance, the vessel probability of each pixel was obtained by averaging multiple predictions. With a stride of 5 pixels in both height and width, multiple consecutive overlapping patches were extracted in each testing image. Then, for each pixel, the vessel probability was obtained by averaging probabilities over all the predicted patches covering the pixel.

An initial image set of 108,859 fundus images that had passed a quality inspection (including 56,626 normal retinas, 2,368 with AMD, 17,045 with moderate to proliferative DR, 21,587 with glaucoma, 7,198 with high myopia, and 4,035 with RVO, and images with cataract) was used to train a machine learning model. Of the diabetic retinopathy images, images were manually labeled with respect to diabetic macular edema. Some images were derived from a cohort of diabetic patients with clinically labeled diabetic kidney dysfunction, defined by a glomerular filtration rate less than 90 ml/min, and some images were clinically reported to have no other diabetic complications. The cohort was approximately evenly split by gender. The racial composition of the patients based on self-reported race/ethnicity was Chinese.

The images were divided into a training data set and a validation data set. Table 1 shows the training data set characteristics with the number of images in each class. Table 2 shows the validation data set characteristics with the number of images in each class.

TABLE 1

Training Set Characteristics.
Training set

|  |  |  |
|---|---|---|
|  | Raw data | 90,335 |
|  | Cleaned data | 49,780 |
| Cleaned data per class | AMD | 3,635 |
|  | DR | 10,686 |
|  | Glaucoma | 8,514 |
|  | HM | 7,803 |
|  | Normal | 14,359 |
|  | RVO | 4,783 |

TABLE 2

Validation data sets characteristics. Number of images used for each class in each validation data set.

| Class | Asian cohort | Caucasian cohort | Brazilian cohort | Hand-held camera |
|---|---|---|---|---|
| AMD | 534 | 6,869 | 245 | 50 |
| DR | 996 | 7,391 | 267 | 50 |
| Glaucoma | 1,029 | 81 | 155 | 50 |
| HM | 1,001 | 2,595 | 216 | 50 |
| Normal | 1,000 | 1,014 | 429 | 50 |
| RVO | 1,013 | 153 | 75 | 42 |
| Total | 5,573 | 18,103 | 1387 | 292 |

Some patients have diabetes but without manifesting any of the signs of diabetes. These patients may be otherwise indistinguishable or difficult to distinguish from healthy patients without any clinical abnormalities. Table 3 shows the data characteristics for diabetic patients without clinical signs of diabetes in comparison to healthy patients.

TABLE 3

Data characteristics for comparing patients with diabetes without any apparent signs of diabetes to healthy patients without any clinical abnormalities.

|  | Train | Test |
|---|---|---|
| NDR | 555 | 98 |
| NORMALNORMAL | 7267 | 93 |

Model Performance

Figure 2A:
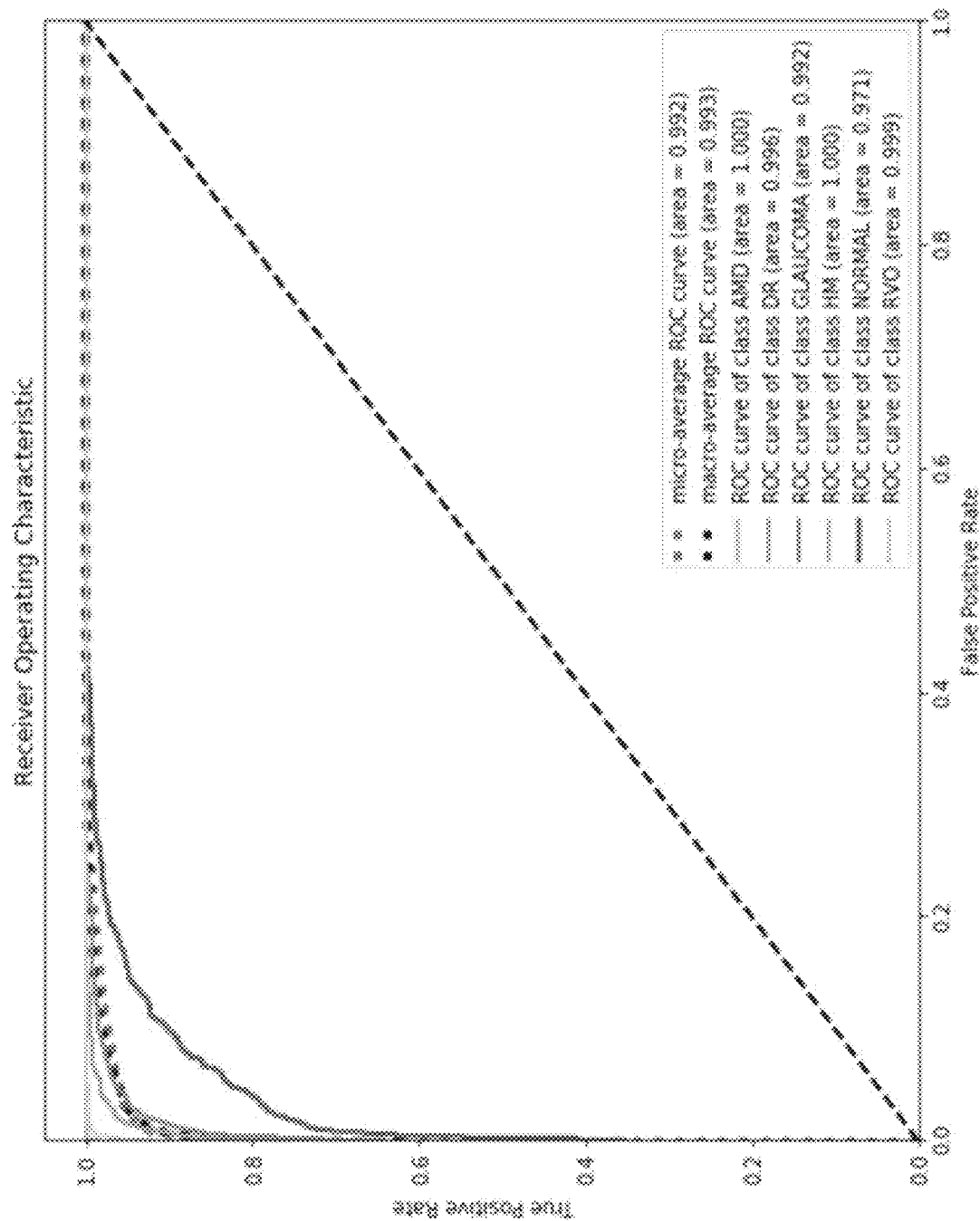
FIGS. 2A-2D show the Receiver Operating Characteristic Curves (ROC) of a multi-class classification model: A) Internal Validation—Asian cohort; B) External validation—Caucasian cohort; C) External validation—Brazilian cohort; and D) External validation—Hand-held camera, according to an embodiment.

The AI system was evaluated for diagnosing the most common blinding eye diseases and was able to accurately classify images with AMD, DR, glaucoma, high myopia (HM), RVO, cataract and normal retinas. After 25 epochs, the training was stopped due to the absence of further improvement in both loss and accuracy. In a multiclass comparison, the model achieved an accuracy of 98.96%. Receiver operating characteristic (ROC) curves were generated to evaluate the model's ability to distinguish each disease. Contributions of each class were aggregated together to produce an average ROC of 99.1% in the Asian cohort without high myopia (FIG. 2A).

Figure 8A:
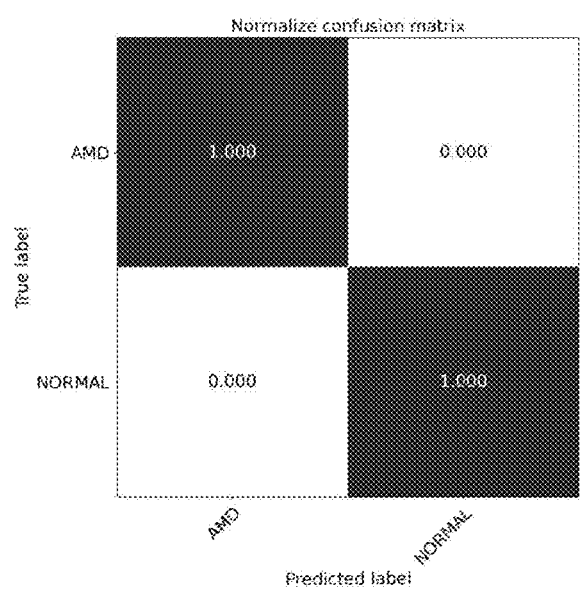
FIGS. 8A-8C show confusion matrices of binary classification Normal x diseases: A) Normal×AMD; B) Normal× DR; C) Normal x Glaucoma; D) Normal x HM; E) Normal x RVO, according to an embodiment.
Figure 8B:
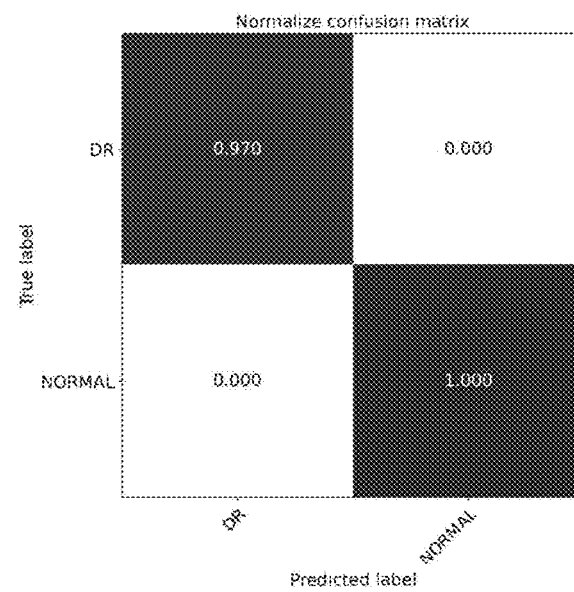
Figure 8C:
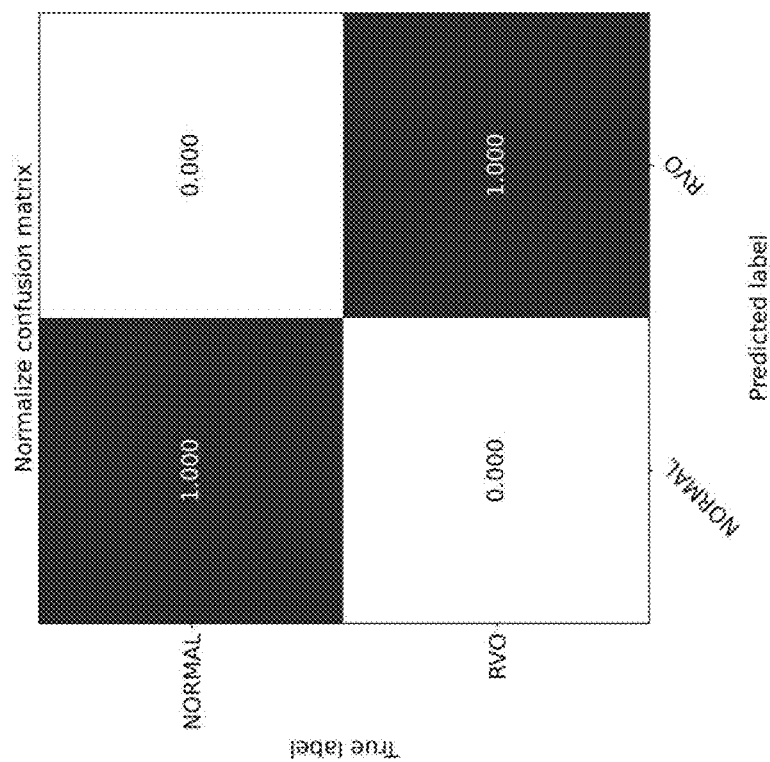
Figure 9A:
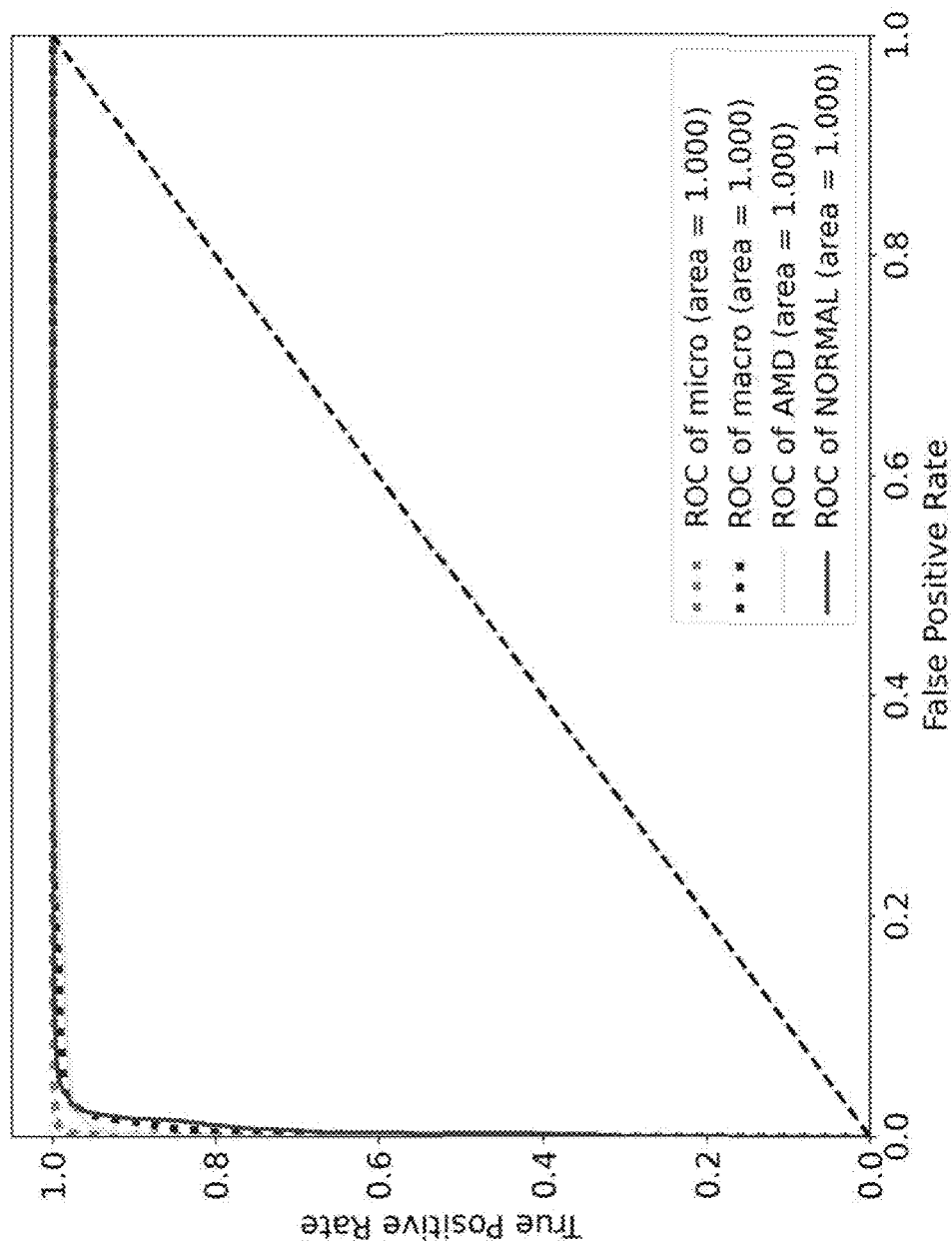
FIGS. 9A-9C show the Receiver Operating Characteristic curves for binary classifiers: A) Normal×AMD; B) Normal× DR; C) Normal×Glaucoma; and D) Normal×RVO, according to an embodiment.
Figure 9B:
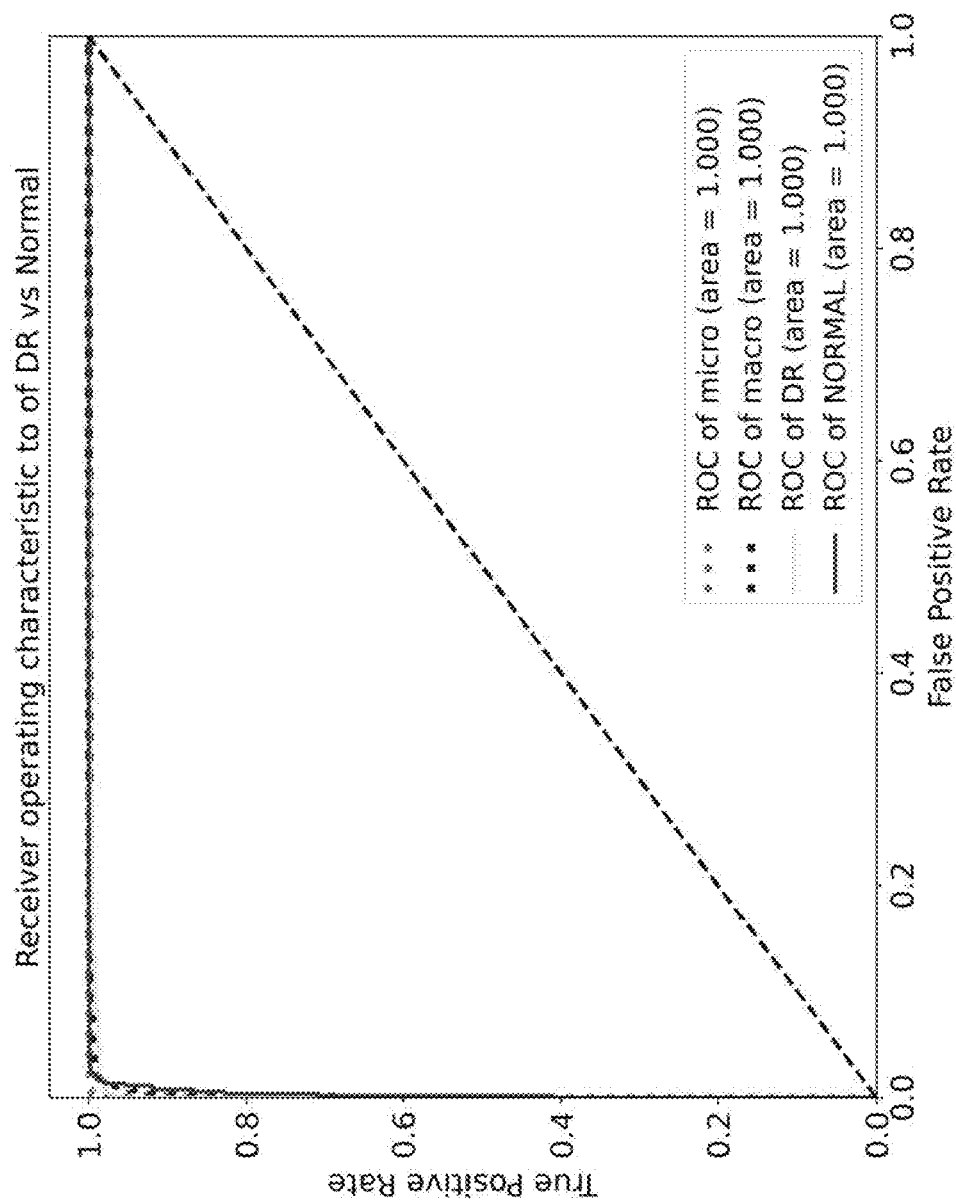
Figure 9C:
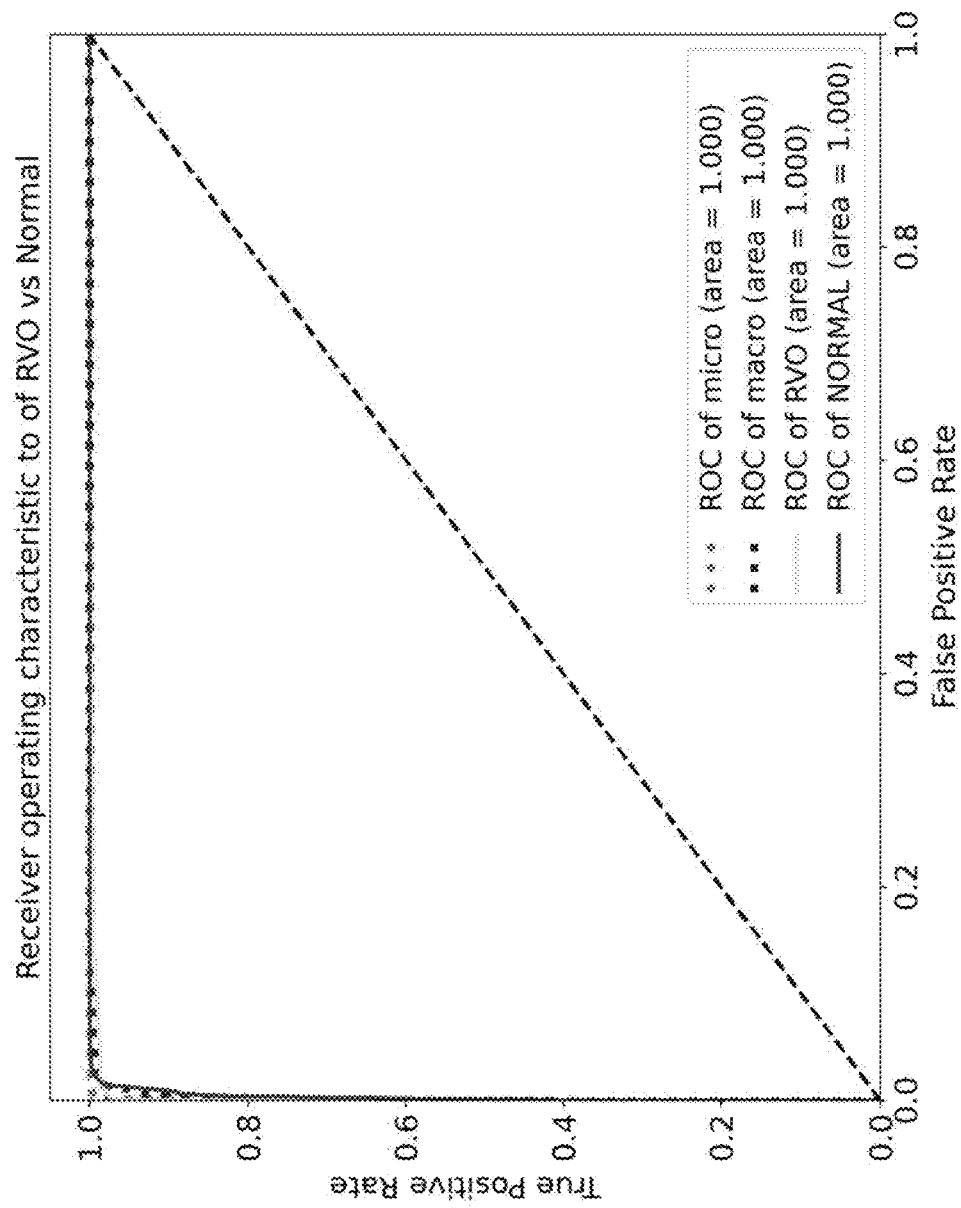

To determine a breakdown of the model's performance, binary classifiers were also implemented. The classifier distinguishing AMD images from normal images achieved an accuracy of 100.0%, with a sensitivity of 100.0% and specificity of 100.0%. (FIG. 8A) The area under the ROC curve (AUC) for the classification of AMD vs normal images was 1.000 (FIG. 9A). The classifier distinguishing DR images from normal images achieved an accuracy of 98.5%, with a sensitivity of 97.0%% and specificity of 100% (FIG. 8B). The AUC was 0.999 (FIG. 9B). The classifier distinguishing glaucoma images from normal images achieved an accuracy of 97.6%, with a sensitivity of 95.3% and specificity of 99.9%. The AUC was 0.996. The classifier distinguishing RVO images from normal images achieved an accuracy of 100.0%, with a sensitivity of 100.0% and specificity of 100.0% (FIG. 8C). The AUC was 1.00 (FIG. 9C).

The model was validated on the Asian cohort and the multi-class comparison produced the following accuracies: 98.3% for AMD, 95.8% for DR, 98.0% for glaucoma, 98.5% for high myopia, 99.2% for normal, and 98.5% for RVO in the Asian cohort (FIG. 1A). The AUC-ROC curves for AMD, DR, glaucoma, HM, normal, and RVO were 1.000, 0.996, 0.992, 1.000, 0.971, and 0.999, respectively (FIG. 2A).

Model Performance in Independent External Validation Cohorts

Figure 2B:
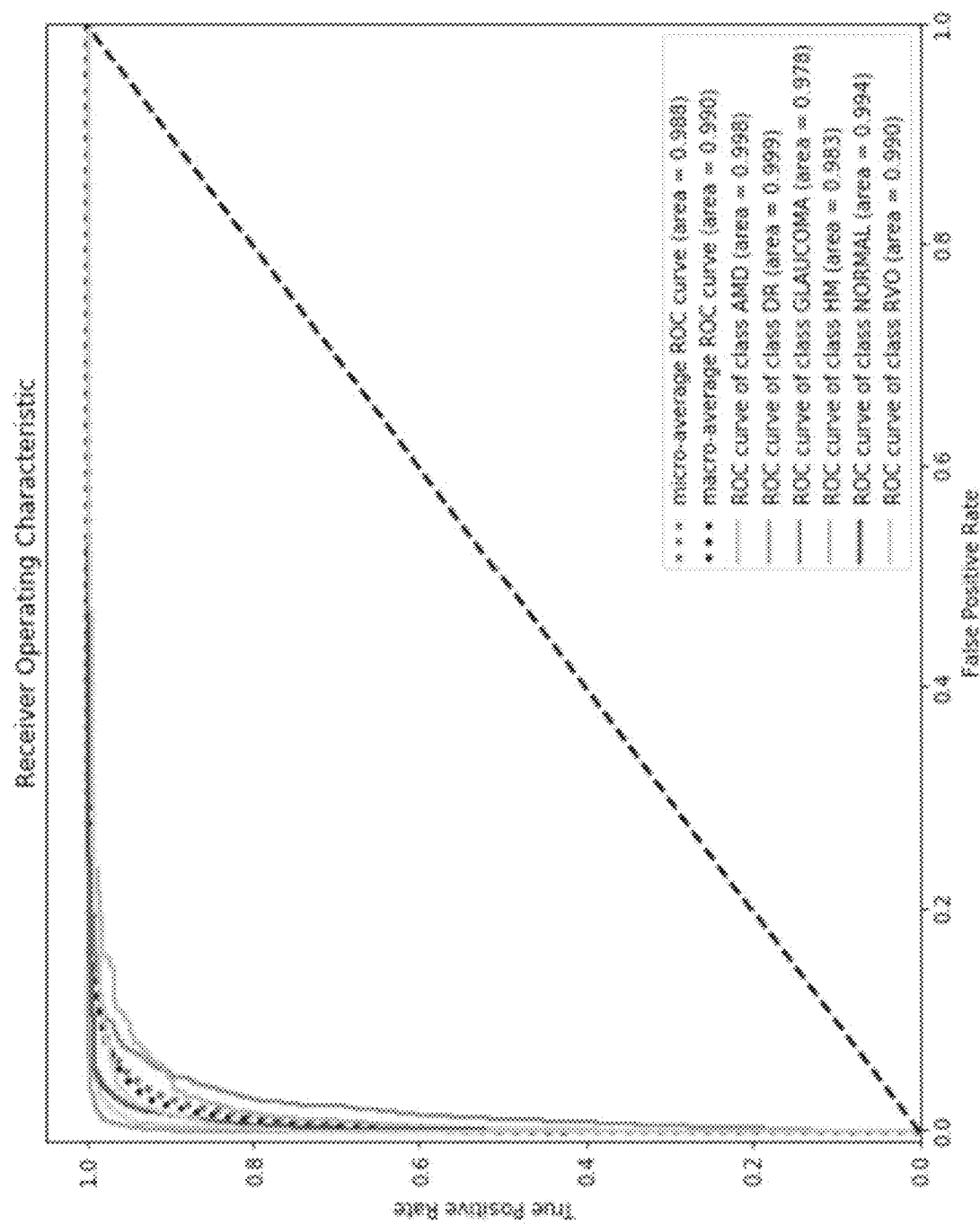

The trained model was externally validated in two independent data sets from separate geographic populations. High accuracies were achieved across all disease phenotypes and therefore demonstrate the applicability of the model across different cohorts. A summary of the cohorts is shown in Table 2. The model was externally validated using a Caucasian cohort consisting of 5,717 images and achieved an accuracy of 94.26%. The multiclass comparison produced the following accuracies: 98.5%, 99.7%, 97.6%, 88.3%, 85.5%, and 92.1% for AMD, DR, glaucoma, HM, normal, and RVO, respectively (FIG. 1B). The AUC-ROC was 0.990 (FIG. 2B). The AUC-ROC curves for AMD, DR, glaucoma, HM, normal, and RVO were 0.998, 0.999, 0.978, 0.963, 0.994, and 0.990, respectively (FIG. 2B).

Figure 2C:
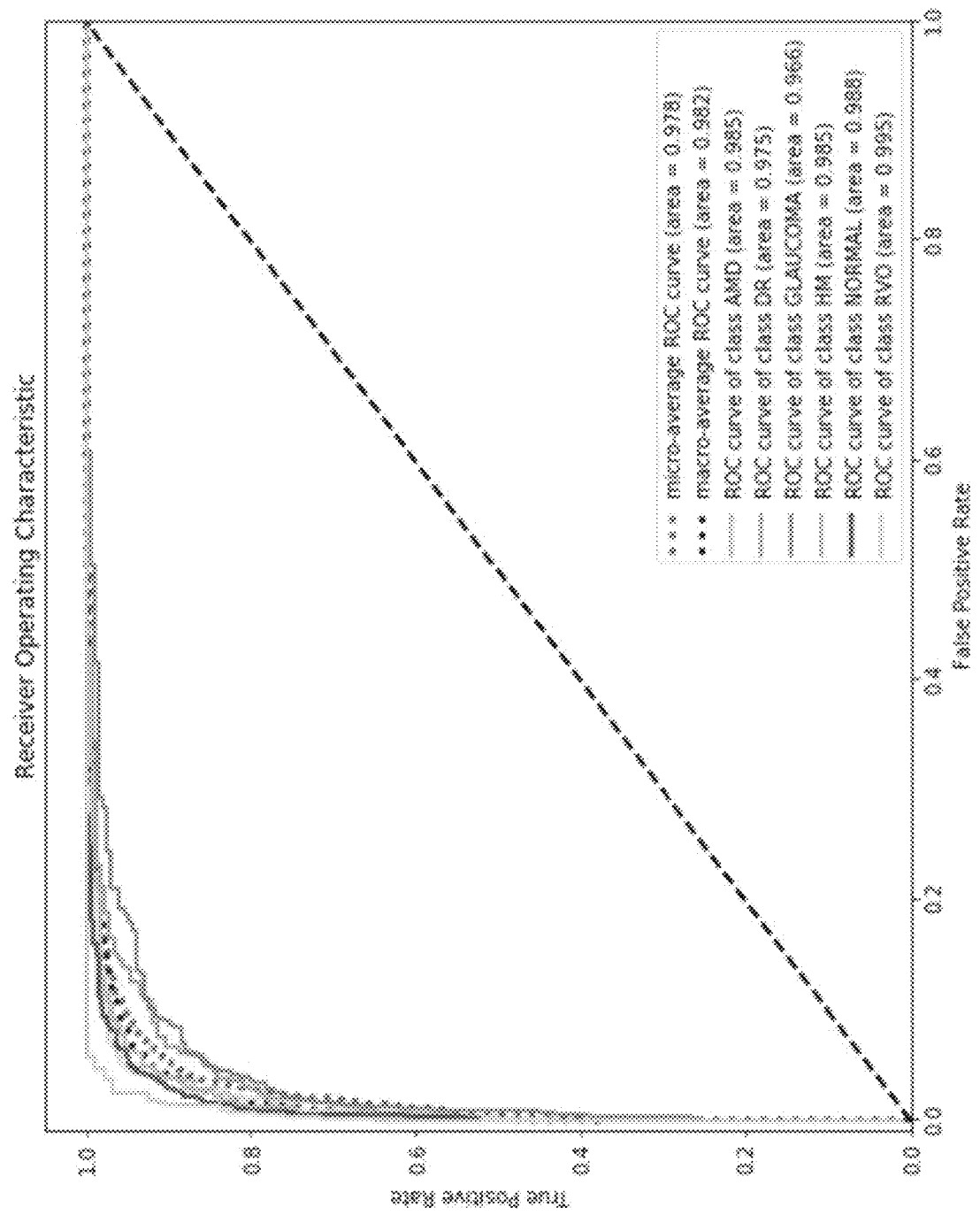

A Brazilian cohort consisting of 1,278 images also underwent external validation and achieved an accuracy of 90.22%. The multiclass comparison produced the following accuracies: 96.8%, 96.9%, 85.8%, 91.3%, 85.7%, and 81.5% for AMD, DR, glaucoma, HM, normal, and RVO, respectively (FIG. 1C). The AUC-ROC was 0.982. (FIG. 2C). The AUC-ROC curves for AMD, DR, glaucoma, HM, normal, and RVO were 0.985, 0.975, 0.966, 0.985, 0.988, and 0.995, respectively (FIG. 2C).

Example 2

Cataract Detection

The algorithm is used to diagnose the presence of cataracts among a cohort of patients presenting with or without cataracts. The model achieves a high accuracy, sensitivity, specificity, and AUC.

Example 3

Comparison of Trained Classifier with Human Experts

A test set of 2960 images, including 500 images within each class, is selected by a team of ophthalmologists to compare the classifications generated by an AI network (trained as in Example 1) to those of independent senior ophthalmologists. Six experts with a mean number of years of experience in both academic and clinical environments are instructed to diagnose each of the fundus images into one of the five disease categories (AMD, DR, glaucoma, HM, RVO), a normal category, and an "other" category. Performance of the model is determined to be similar to that of expert physicians.

Example 4

Detection of Diabetes

Figure 3A:
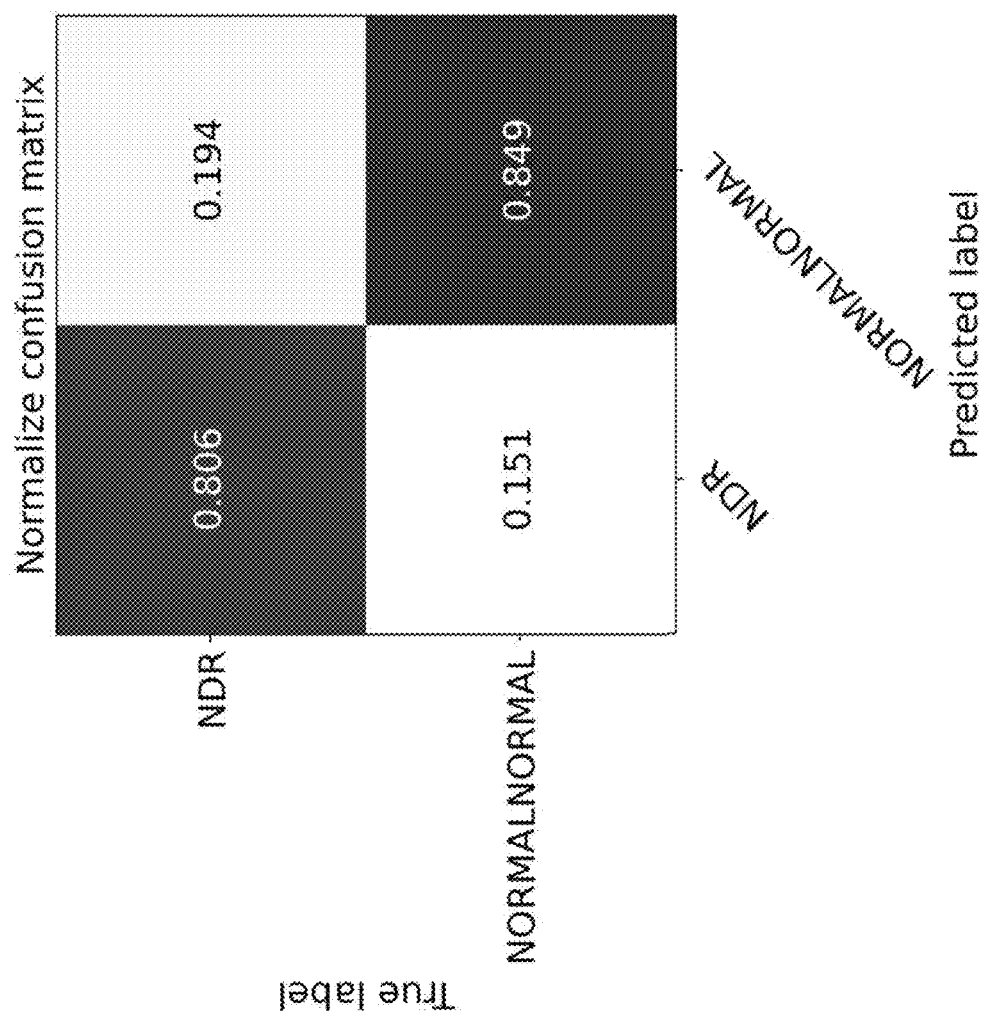
FIGS. 3A and 3B show a confusion matrix comparing diabetes without retinopathy to healthy patients, according to an embodiment.
Figure 3B:
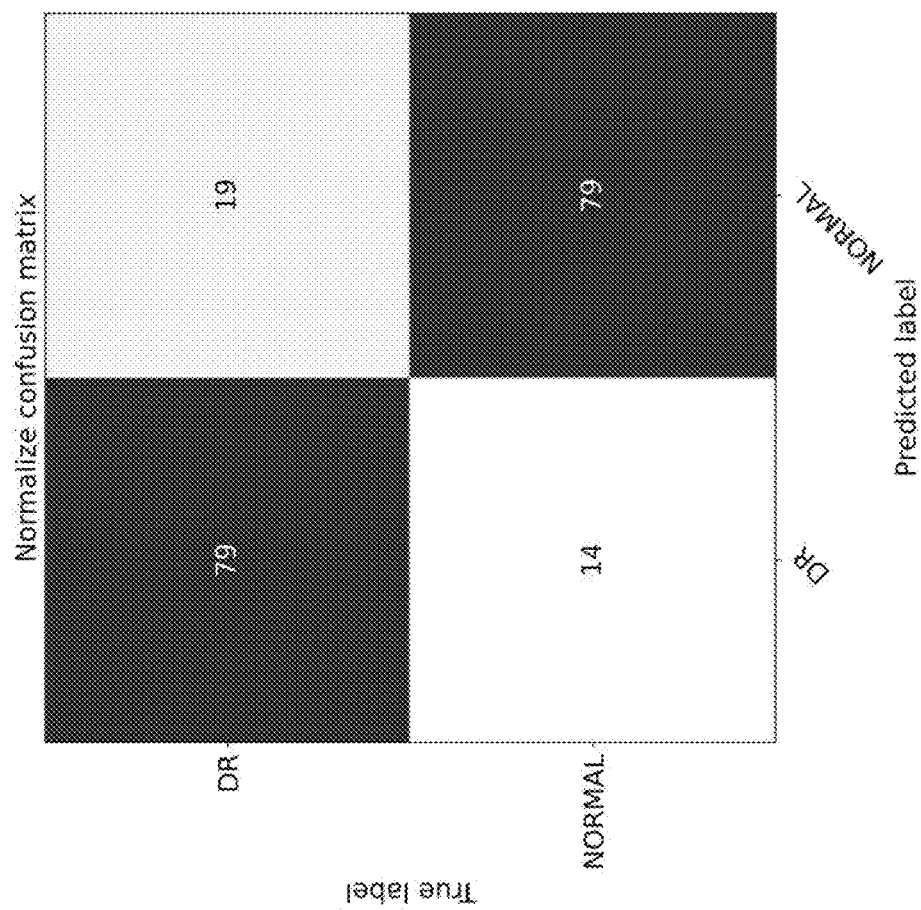
Figure 4:
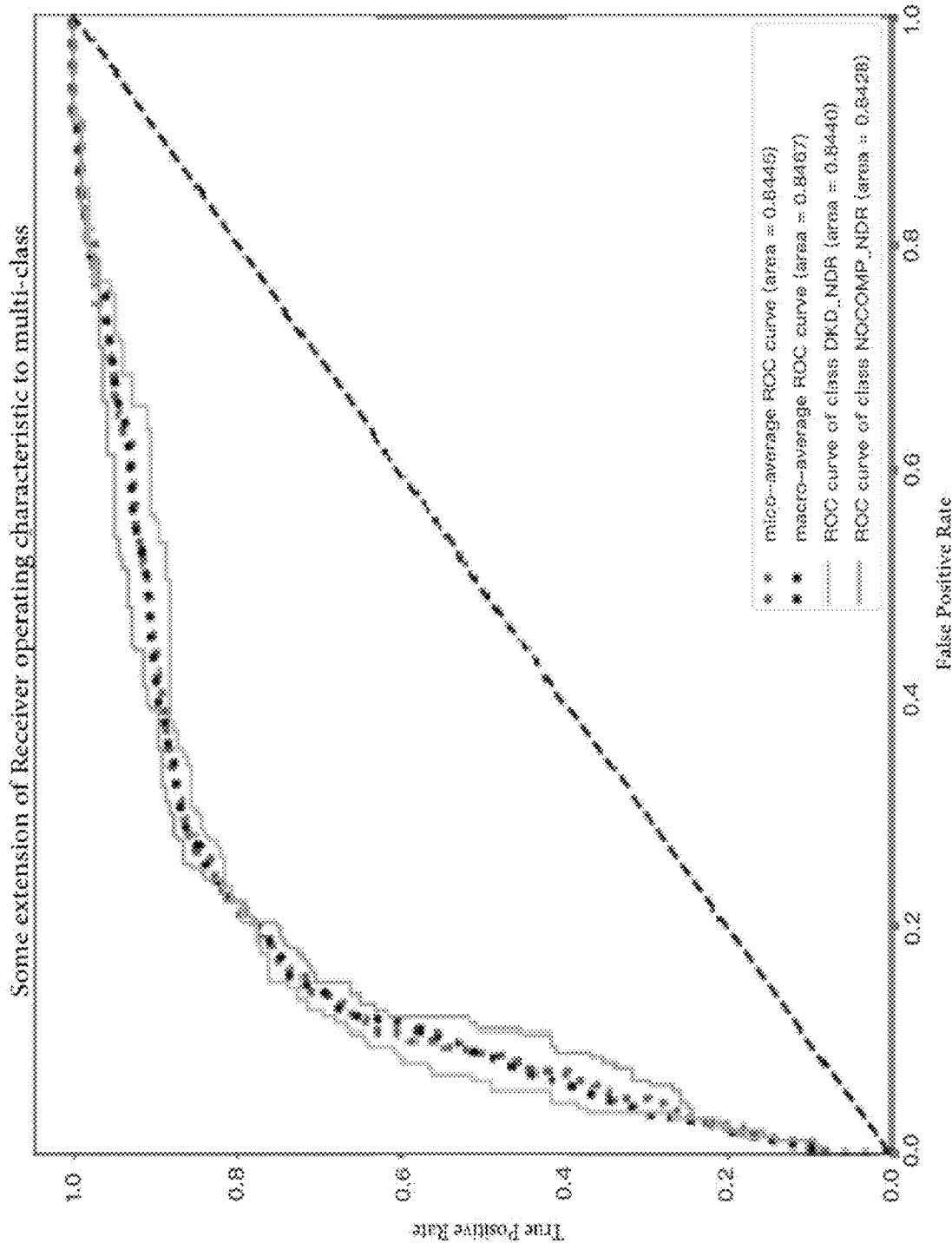
FIG. 4 shows the ROC of diabetes without retinopathy compared to healthy patients, according to an embodiment.
Figure 5B:
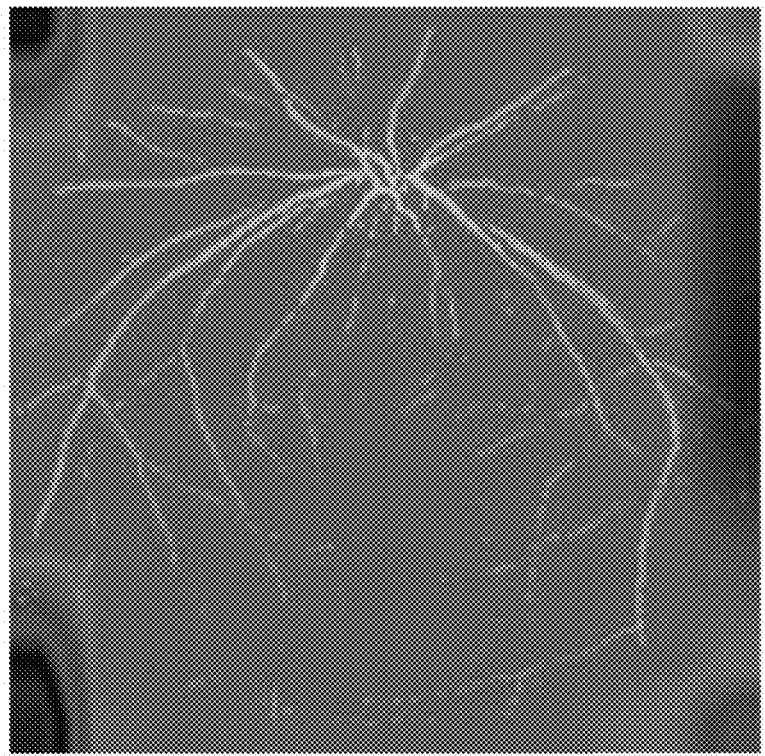
FIGS. 5A and 5B show visualizations for vessel segmentation in comparing diabetes without retinopathy compared to healthy patients without any clinical manifestations, according to an embodiment.
Figure 5A:
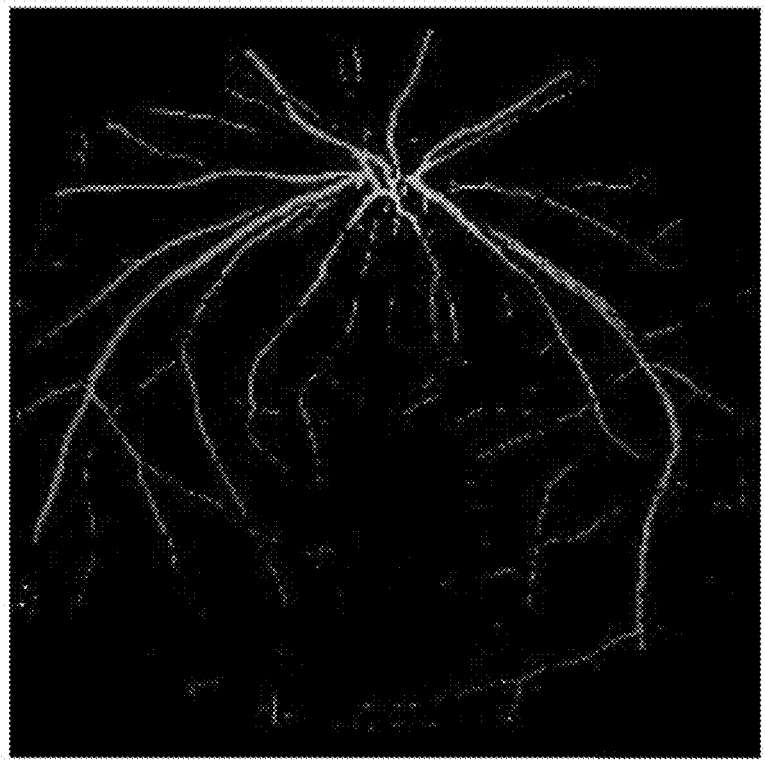

The model was trained and evaluated for its ability to identify important systemic conditions by isolating the vasculature through vessel segmentation. First, the images from nondiabetic patients, defined by normal glycosylated hemoglobin (HbA1C) 1 levels with no history of diabetes, were compared against diabetic patients without retinopathy, defined by HbA1c levels of 6.5% or higher but with no apparent retinal abnormalities. The model achieved an accuracy of 82.7%, with a sensitivity of 80.6%, and a specificity of 84.9% as shown on the normalized confusion matrix in FIG. 3A, and an area under the ROC curve of 0.867 (FIG. 4). The confusion matrix without normalization showing the number of images in each category is in FIG. 3B. The visualization of the vessel segmentation can be seen in FIGS. 5A and 5B. The model therefore shows strong performance in identifying diabetic patients before the onset of disease manifestations in the retina and therefore could potentially serve as a valuable diabetic screening tool.

Example 5

Detection of Diabetic Kidney Disease

Figure 6:
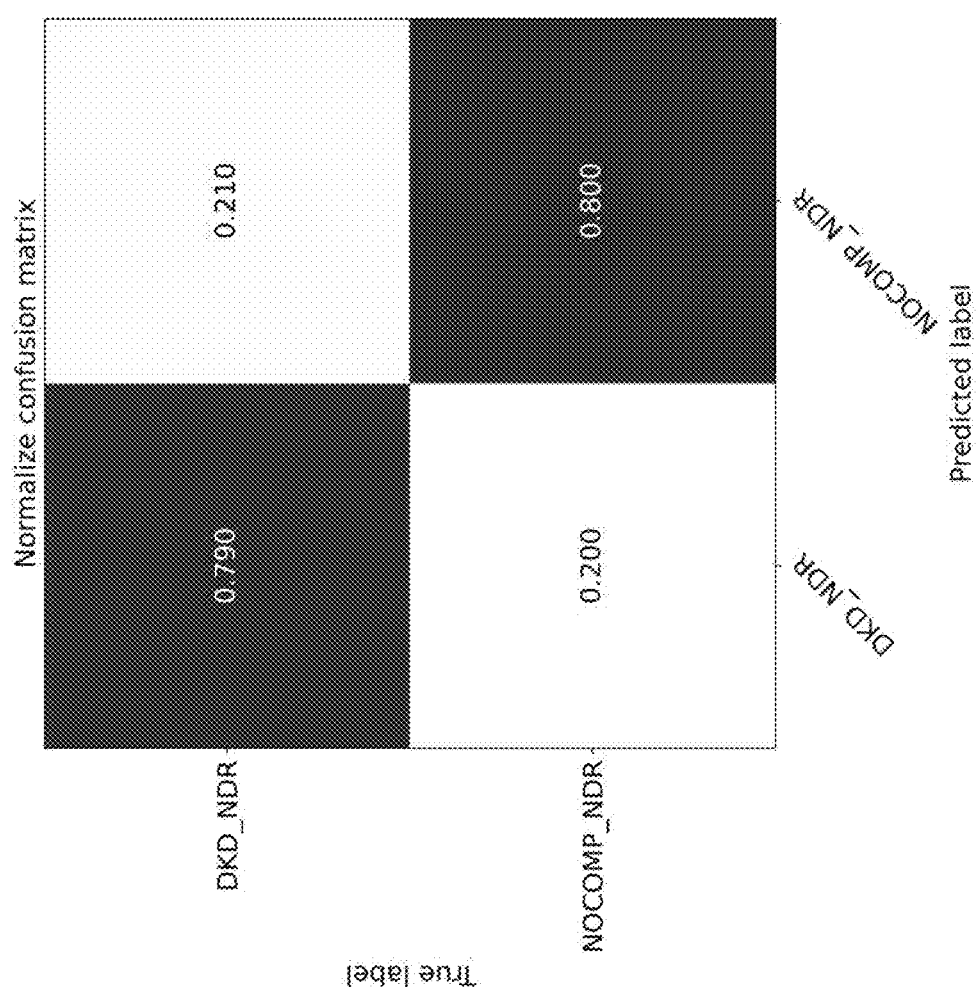
FIG. 6 shows a confusion matrix comparing patients with diabetes without retinopathy and without complications (NOCOMP) vs. patients with diabetes without retinopathy but with diabetic kidney disease (DKD), according to an embodiment.
Figure 7:
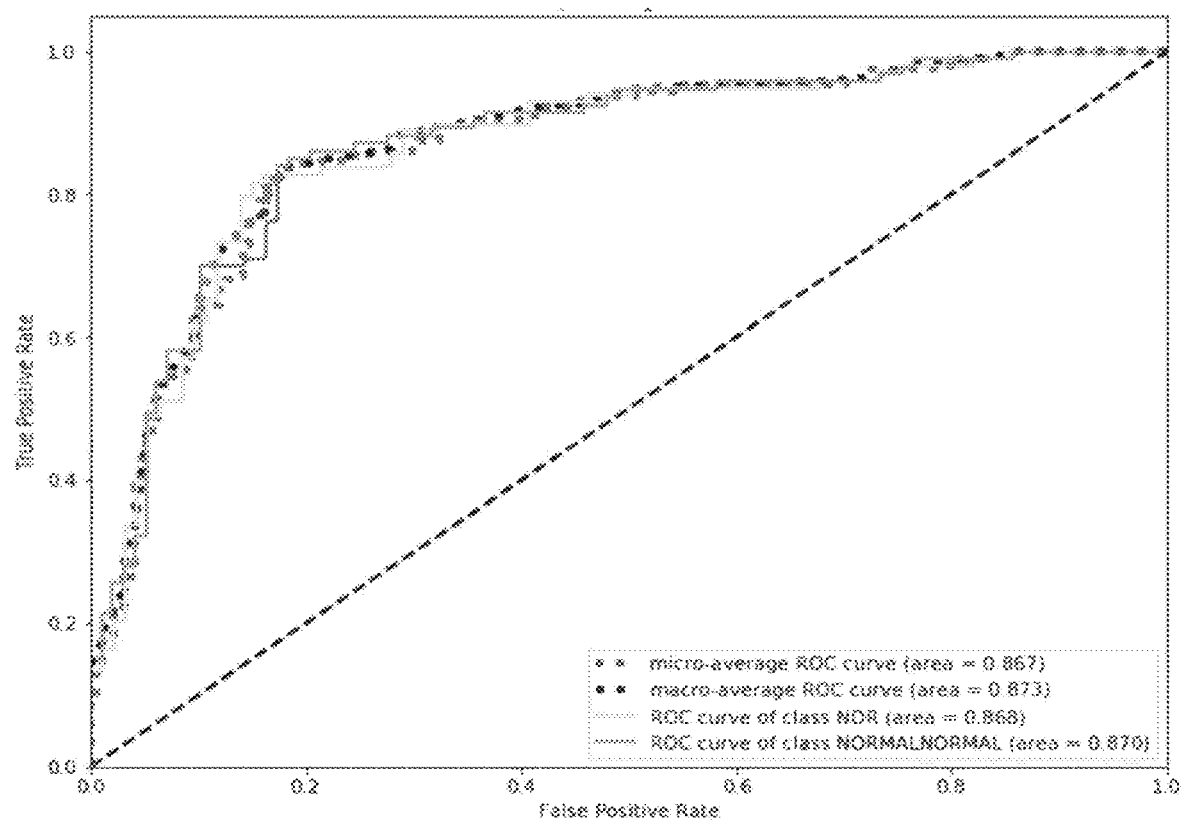
FIG. 7 shows the ROC comparing patients with diabetes without retinopathy and without complications (NOCOMP) vs. patients with diabetes without retinopathy but with diabetic kidney disease (DKD), according to an embodiment.
Figure 10A:
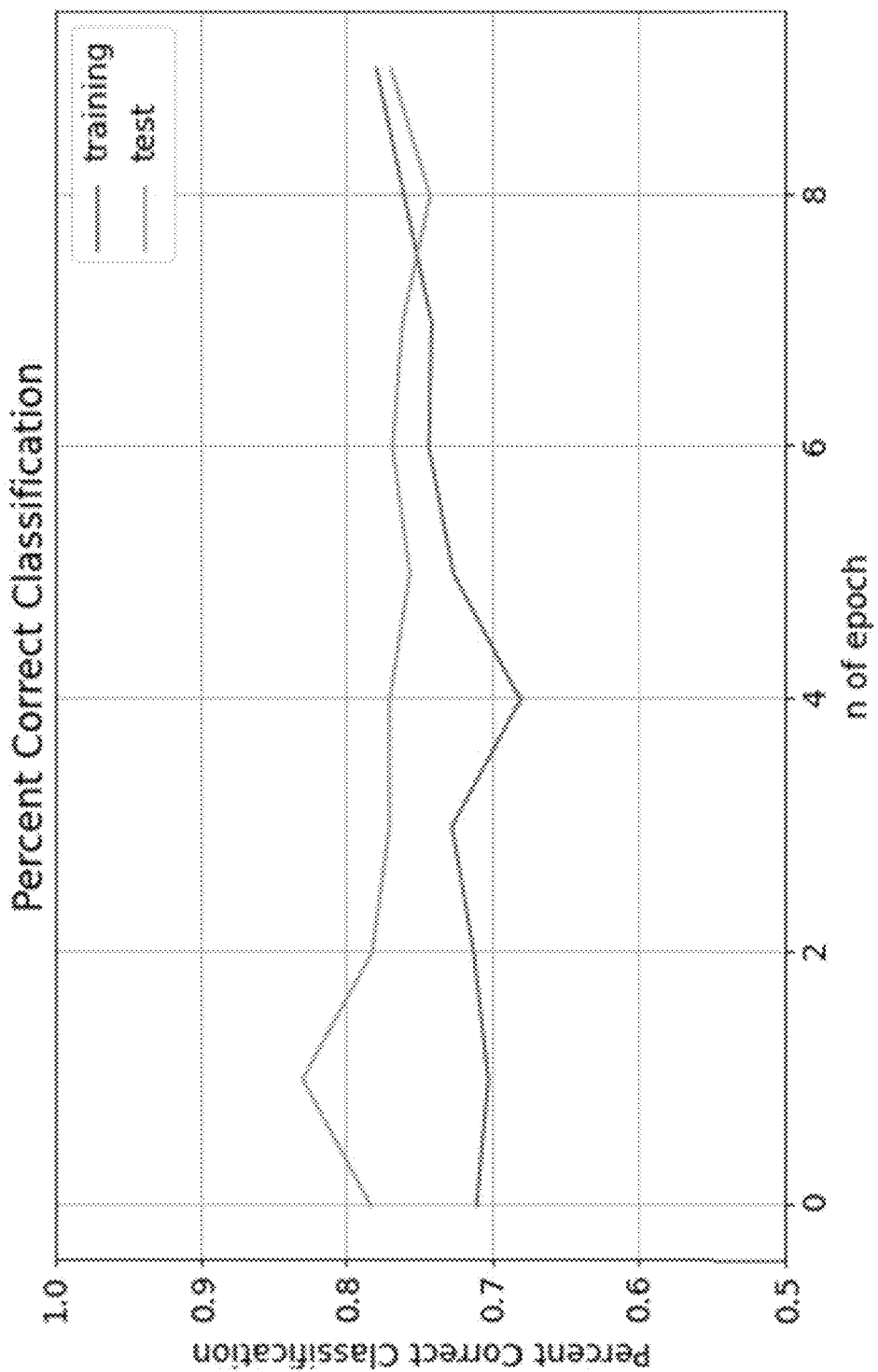
FIGS. 10A and 10B show model accuracy and loss over time, respectively, for detection of diabetic kidney disease, according to an embodiment.
Figure 10B:
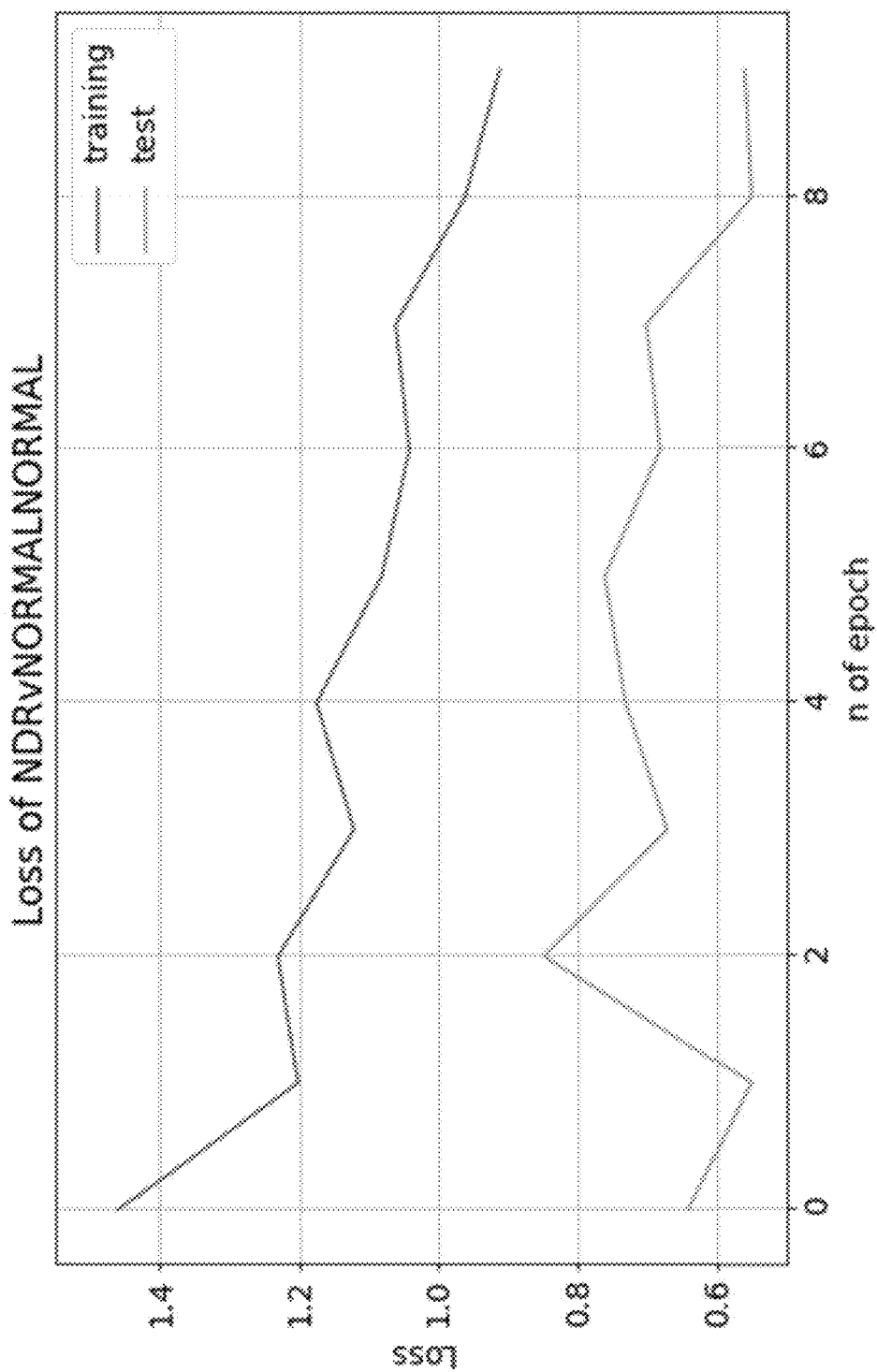

The model was trained and evaluated for its ability to distinguish diabetic patients with kidney disease from ones without kidney complication. Fundus images obtained from patients clinically defined as diabetic without other systemic complications were compared to patients with diabetic kidney disease. In comparing these patients who lack any retinopathy, the model was able to predict diabetic kidney disease with 79.25% accuracy, 79% sensitivity, and 80% specificity (FIG. 6) The area under the ROC curve was 0.873 (FIG. 7). Model accuracy and loss over time can be seen in FIGS. 10A and 10B, respectively.

Example 6

Detection of Cardiovascular Risk

The model is trained and evaluated for its ability to diagnose patients at cardiovascular risk, defined by systolic and/or diastolic pressure values greater than 140 and 90 mmHg respectively, cholesterol values greater than a threshold, and with apparent hypertensive retinopathy features, against patients with normal blood pressure and cholesterol values. Results show that the model is able to effectively classify at-risk patients with a high level of accuracy, sensitivity, and specificity, and AUC.

Example 7

Detection of Stroke

The model is trained and evaluated for its ability to detect stroke. Results show that the model is able to effectively classify at-risk patients with a high level of accuracy, sensitivity, and specificity, and AUC.

Example 8

Software Integrated Into Hardware

Diagnostic software implementing deep learning convolutional neural networks for analyzing retinal scans to screen for common eye and systemic diseases are installed onto systems integrating imaging equipment and computing devices at a medical clinic. The computing devices are operatively coupled to the imaging equipment including stereoscopic color fundus photography. During a patient visit, the imaging equipment is used to capture an ophthalmic image of both retinas. The image is stored locally on the computing device operatively coupled to the imaging equipment. The software application installed on the computing device then analyzes the image using a trained convolutional neural network to classify the image as being positive or negative for diabetes (e.g., without signs of diabetic retinopathy detectable by a clinician). The application uploads the image to a remote server over the network for remote classification or prediction and downloads the result. When communication with the remote server is unavailable, the software application is configured to perform the analysis using the locally stored convolutional neural network.

Example 9

Portable Diagnostic System

Diagnostic software implementing deep learning convolutional neural networks for analyzing retinal scans to screen for common eye and systemic diseases are installed onto a user's smartphone as a mobile application. The mobile application enables the smartphone to upload retinal scans for remote diagnosis. The mobile application also allows the smartphone to integrate imaging equipment to capture the retinal image using the smartphone's own camera. An apparatus comprising an ophthalmoscope is detachably coupled to the smartphone such that the ophthalmoscope is positioned over the smartphone camera enabling the camera to capture the desired retinal scan. The retinal scan image is stored locally on the smartphone. The mobile application installed on the phone then analyzes the image using a trained convolutional neural network to classify the image as being positive or negative for diabetes. The analysis includes uploading the image to a remote server over the network for remote classification or prediction and downloading the result. When communication with the remote server is unavailable, the mobile application is configured to perform the analysis using the locally stored convolutional neural network. Accordingly, this portable diagnostic system leverages the smartphone's electronics and camera in combination with the apparatus and ophthalmoscope to efficiently capture retinal scans and obtain diagnostic predictions.

Example 10

Diagnostic Hardware

A diagnostic device comprising a specialized camera and a digital processing device is utilized to capture an ophthalmic image of a retina and generate a diagnostic prediction of a common eye or systemic disease. The device includes a specialized camera designed to capture retinal scans, which are stored on a memory of the digital processing device and subsequently analyzed by the device. The software application installed on the digital processing device analyzes the image using a trained convolutional neural network to classify the image as being positive or negative for diabetic retinopathy. The analysis includes uploading the image to a remote server over the network for remote classification or prediction and downloading the result. When communication with the remote server is unavailable, the software application is configured to perform the analysis using the locally stored convolutional neural network.

Example 11

Point-of-Care Diagnosis of Common Eye Diseases Using a Smart Phone System

Figure 1D:
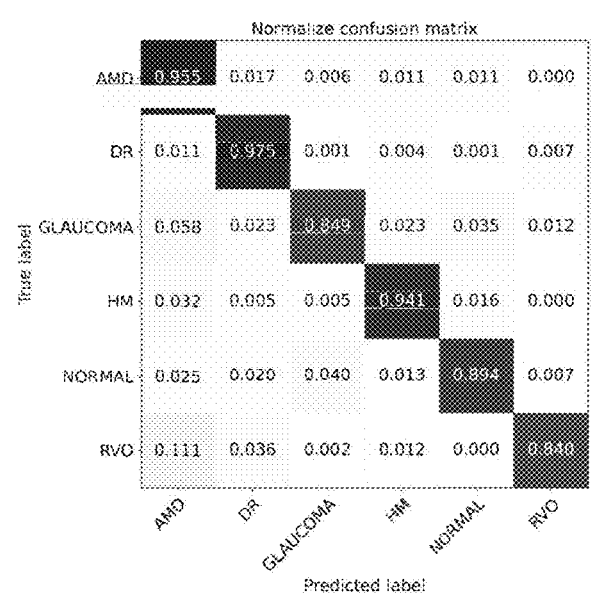
Figure 2D:
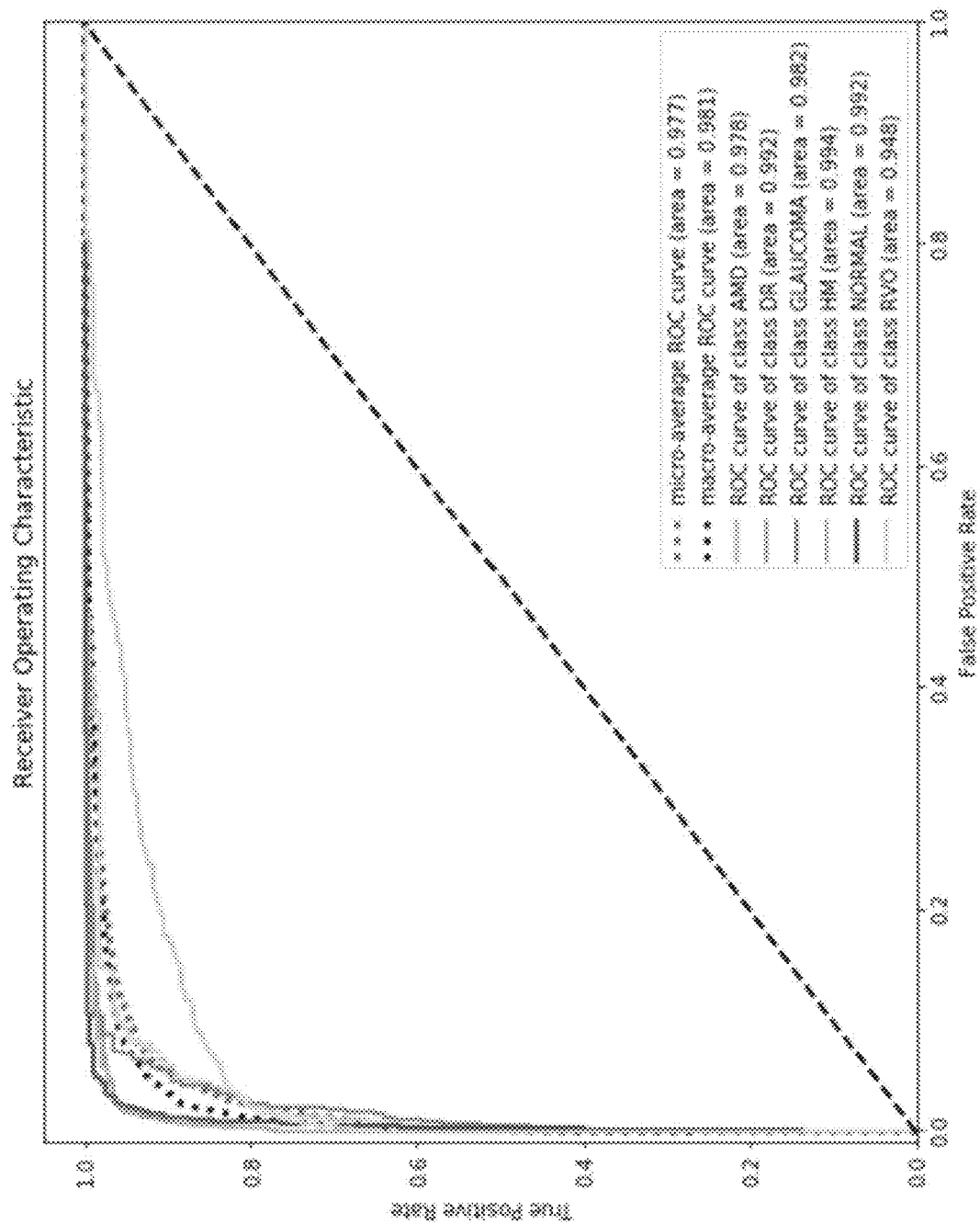

A low-cost hand-held camera smartphone attachment was built. In addition, an IOS application was programmed to act as an interface between the user's smartphone camera and the AI platform. In this effort, patients can easily upload their own fundus images to the HIPPA-compliant cloud service where the AI model could autonomously grade incoming diagnostic requests. While the model was trained from standard fundus imaging machines, the model showed surprising adaptability to real-world applications. The hand-held camera attachment served as an external validation and produced an accuracy of 91.83%. The multiclass comparison produced the following accuracies: 95.5%, 97.5%, 84.9%, 94.1%, 89.4%, 84.0% for AMD, DR, Glaucoma, HM, Normal, and RVO, respectively (FIG. 1D). The AUC-ROC was 0.981. (FIG. 2D).

Example Non-Limiting Embodiments

Non-limiting examples of some embodiments are as follows:

A computer-implemented method for analyzing ophthalmic imaging data obtained from a subject to determine the presence of an ophthalmic or systemic disease, disorder, or condition, the method comprising: obtaining the ophthalmic imaging data; and processing the ophthalmic imaging data with an algorithm comprising a classifier trained using a machine learning procedure to output a determination of the presence of the ophthalmic or systemic disease, disorder, or condition. The determination has a sensitivity of at least 90% and a specificity of at least 90%. The determination has an AUC of at least 0.9. The machine learning procedure comprises training a model using a deep learning procedure to generate the classifier. The classifier is a convolutional neural network. The machine learning procedure comprises performing a transfer learning procedure to generate the classifier. The transfer learning procedure comprises pre-training a neural network using non-domain images, freezing at least one feature layer of the neural network, and training the neural network using domain images. The method further comprises making a medical treatment recommendation based on the determination. The ophthalmic imaging data comprises an ophthalmic image. The ophthalmic image is a retinal image. The ophthalmic image is a fundus image. The ophthalmic disease or disorder is selected from the group consisting of age-related macular degeneration, diabetic retinopathy, glaucoma, cataract, myopia, retinal vein occlusions, kidney disease, hypertension, and stroke. The subject has not manifested visible abnormalities or symptoms of the ophthalmic or systemic disease, disorder, or condition at the time the ophthalmic imaging data was generated.

A computer-implemented system configured for analyzing ophthalmic imaging data obtained from a subject to determine the presence of an ophthalmic or systemic disease, disorder, or condition, the system comprising: an electronic device comprising: a processor, a memory, a display, a camera, and an operating system configured to perform executable instructions; a computer program stored in the memory of the electronic device, the computer program including instructions executable by the user electronic device to create an application comprising: a software module obtaining the ophthalmic imaging data; and a software module processing the ophthalmic imaging data with an algorithm comprising a classifier trained using a machine learning procedure to output a determination of the presence of the ophthalmic or systemic disease, disorder, or condition. The determination has a sensitivity of at least 90% and a specificity of at least 90%. The determination has an AUC of at least 0.9. The machine learning procedure comprises training a model using a deep learning procedure to generate the classifier. The classifier is a convolutional neural network. The machine learning procedure comprises performing a transfer learning procedure to generate the classifier. The transfer learning procedure comprises pre-training a neural network using non-domain images, freezing at least one feature layer of the neural network, and training the neural network using domain images. The application further comprises a software module making a medical treatment recommendation based on the determination. The ophthalmic imaging data comprises an ophthalmic image. The ophthalmic image is a retinal image. The ophthalmic image is a fundus image. The ophthalmic disease or disorder is selected from the group consisting of age-related macular degeneration, diabetic retinopathy, glaucoma, cataract, myopia, retinal vein occlusions, kidney disease, hypertension, and stroke. The subject has not manifested visible abnormalities or symptoms of the ophthalmic or systemic disease, disorder, or condition at the time the ophthalmic imaging data was generated.

A non-transitory computer-readable medium comprising machine-executable code that, upon execution by one or more computer processors, implements a method for processing ophthalmic imaging data, the method comprising: obtaining the ophthalmic imaging data; and processing the ophthalmic imaging data with an algorithm comprising a classifier trained using a machine learning procedure to output a determination of the presence of the ophthalmic or systemic disease, disorder, or condition. The determination has a sensitivity of at least 90% and a specificity of at least 90%. The determination has an AUC of at least 0.9. The machine learning procedure comprises training a model using a deep learning procedure to generate the classifier. The classifier is a convolutional neural network. The machine learning procedure comprises performing a transfer learning procedure to generate the classifier. The transfer learning procedure comprises pre-training a neural network using non-domain images, freezing at least one feature layer of the neural network, and training the neural network using domain images. The application further comprises a software module making a medical treatment recommendation based on the determination. The ophthalmic imaging data comprises an ophthalmic image. The ophthalmic image is a retinal image. The ophthalmic image is a fundus image. The ophthalmic disease or disorder is selected from the group consisting of age-related macular degeneration, diabetic retinopathy, glaucoma, cataract, myopia, retinal vein occlusions, kidney disease, hypertension, and stroke. The subject has not manifested visible abnormalities or symptoms of the ophthalmic or systemic disease, disorder, or condition at the time the ophthalmic imaging data was generated.

A computer-implemented system comprising: an electronic device comprising: a processor, a memory, a display, a camera, and an operating system configured to perform executable instructions; a portable device comprising an imaging component, said portable device configured to receive and position the electronic device to align the camera with the imaging component for capturing ophthalmic imaging data; and a computer program stored in the memory of the electronic device, the computer program including instructions executable by the user electronic device to create an application comprising: a software module obtaining the ophthalmic imaging data; and a software module processing the ophthalmic imaging data with an algorithm comprising a classifier trained using a machine learning procedure to output a determination of a presence of an ophthalmic or systemic disease, disorder, or condition. Processing the ophthalmic imaging data comprises uploading the ophthalmic image or video to a cloud network to be analyzed by the trained classifier. The ophthalmic imaging data comprises a retinal image or video captured by the electronic device using the portable device comprising the imaging component. The determination has a sensitivity of at least 90% and a specificity of at least 90%. The determination has an AUC of at least 0.9. The machine learning procedure comprises training a model using a deep learning procedure to generate the classifier. The classifier is a convolutional neural network. The machine learning procedure comprises performing a transfer learning procedure to generate the classifier. The transfer learning procedure comprises pre-training a neural network using non-domain images, freezing at least one feature layer of the neural network, and training the neural network using domain images. The application further comprises a software module making a medical treatment recommendation based on the determination. The system as described herein, wherein the ophthalmic imaging data comprises an ophthalmic image. The ophthalmic image is a retinal image. The ophthalmic image is a fundus image. The ophthalmic disease or disorder is selected from the group consisting of age-related macular degeneration, diabetic retinopathy, glaucoma, cataract, myopia, retinal vein occlusions, kidney disease, hypertension, and stroke. The subject has not manifested visible abnormalities or symptoms of the ophthalmic or systemic disease, disorder, or condition at the time the ophthalmic imaging data was generated. The imaging component is an ophthalmoscope enabling the camera to capture the ophthalmic image or video from an eye of a subject. The portable device comprises an adaptor configured to receive and position the electronic device. The electronic device is a smartphone or a tablet.

A computer-implemented system comprising: a medical imaging device configured to capture an ophthalmic image of a subject; an electronic device operatively coupled to the medical imaging device, comprising: a processor, a memory, a display, and an operating system configured to perform executable instructions; a computer program stored in the memory of the electronic device, the computer program including instructions executable by the user electronic device to create an application comprising: a software module obtaining the ophthalmic imaging data; and a software module processing the ophthalmic imaging data with an algorithm comprising a classifier trained using a machine learning procedure to output a determination of a presence of an ophthalmic or systemic disease, disorder, or condition. Processing the ophthalmic imaging data comprises uploading the ophthalmic image or video to a cloud network to be analyzed by the trained classifier. The determination has a sensitivity of at least 90% and a specificity of at least 90%. The determination has an AUC of at least 0.9. The machine learning procedure comprises training a model using a deep learning procedure to generate the classifier. The classifier is a convolutional neural network. The machine learning procedure comprises performing a transfer learning procedure to generate the classifier. The transfer learning procedure comprises pre-training a neural network using non-domain images, freezing at least one feature layer of the neural network, and training the neural network using domain images. The application further comprises a software module making a medical treatment recommendation based on the determination. The ophthalmic imaging data comprises an ophthalmic image. The ophthalmic image is a retinal image. The ophthalmic image is a fundus image. The ophthalmic disease or disorder is selected from the group consisting of age-related macular degeneration, diabetic retinopathy, glaucoma, cataract, myopia, retinal vein occlusions, kidney disease, hypertension, and stroke. The subject has not manifested visible abnormalities or symptoms of the ophthalmic or systemic disease, disorder, or condition at the time the ophthalmic imaging data was generated. The medical imaging device comprises an ophthalmoscope and a fundus camera. The portable device comprises an adaptor configured to receive and position the electronic device. The electronic device is a smartphone or a tablet. The system is configured as a self-service kiosk. The kiosk comprises a positioning component for positioning a head of a subject in front of the medical imaging device to capture the ophthalmic image. The positioning component is configured to reduce or minimize head tilt by the subject. The kiosk further comprises a microphone and a speaker, and is configured to provide teleconferencing with a remote healthcare provider to discuss the determination and optionally a treatment recommendation. The kiosk comprises an interface for receiving payment information. The interface comprises a card reader, a scanner, an RFID system, a cash acceptor, a touchscreen for entering payment information, or a combination thereof.

A computer-implemented method for analyzing a fundus image obtained from a subject to determine the presence of an ophthalmic or systemic disease or disorder, the method comprising: obtaining the fundus image; and processing the fundus image with an algorithm comprising a classifier trained using a machine learning procedure to output a determination of the presence of the ophthalmic or systemic disease or disorder, wherein the subject does not exhibit visible abnormalities or symptoms of the ophthalmic or systemic disease or disorder.

A computer-implemented system configured for analyzing a fundus image obtained from a subject to determine the presence of an ophthalmic or systemic disease or disorder, the system comprising: an electronic device comprising: a processor, a memory, a display, a camera, and an operating system configured to perform executable instructions; a computer program stored in the memory of the electronic device, the computer program including instructions executable by the user electronic device to create an application comprising: a software module obtaining the fundus image; and a software module processing the fundus image with an algorithm comprising a classifier trained using a machine learning procedure to output a determination of the presence of the ophthalmic or systemic disease or disorder.

A non-transitory computer-readable medium comprising machine-executable code that, upon execution by one or more computer processors, implements a method for processing a fundus image, the method comprising: obtaining the fundus image; and processing the fundus image with an algorithm comprising a classifier trained using a machine learning procedure to output a determination of the presence of the ophthalmic or systemic disease or disorder.

A computer-implemented system comprising: an electronic device comprising: a processor, a memory, a display, a camera, and an operating system configured to perform executable instructions; a portable device comprising an imaging component, said portable device configured to receive and position the electronic device to align the camera with the imaging component for capturing a fundus image; and a computer program stored in the memory of the electronic device, the computer program including instructions executable by the user electronic device to create an application comprising: a software module obtaining the fundus image; and a software module processing the fundus image with an algorithm comprising a classifier trained using a machine learning procedure to output a determination of a presence of an ophthalmic or systemic disease or disorder.

A computer-implemented system comprising: a medical imaging device configured to capture a fundus image of an eye of a subject; an electronic device operatively coupled to the medical imaging device, comprising: a processor, a memory, a display, and an operating system configured to perform executable instructions; a computer program stored in the memory of the electronic device, the computer program including instructions executable by the user electronic device to create an application comprising: a software module obtaining the fundus image; and a software module processing the fundus image with an algorithm comprising a classifier trained using a machine learning procedure to output a determination of a presence of an ophthalmic or systemic disease or disorder.

Embodiment 1: A method comprising using at least one hardware processor to: receive ophthalmic image data; apply a machine-learning classifier, trained using a domain dataset of ophthalmic images that have been labeled with one or more of a plurality of classifications, to classify the received ophthalmic image data into at least one of the plurality of classifications, wherein the plurality of classifications comprise a normal classification and one or more disorder classifications, wherein the one or more disorder classifications comprise at least one of age-related macular degeneration (AMD), diabetic retinopathy (DR), glaucoma, or retinal vein occlusion (RVO); and provide a report that indicates the at least one classification of the received ophthalmic image data.

Embodiment 2: The method of Embodiment 1, wherein, within the dataset, the normal classification is defined as optic discs presenting with sharp margins and a cup-to-disc ratio within a predetermined range, striated sheen from a healthy retinal nerve fiber layer, no lesions, no apparent sub-retinal disruptions, no pigmentary changes, no tumors, no scars, no molds, and normal vasculature, with an exception for drusens indicative of normal age progression.

Embodiment 3: The method of either Embodiment 1 or 2, wherein, within the dataset, the normal classification is defined as no clinically abnormal features, no known ocular disease, and hemoglobin A1C levels less than 6.0%, with an exception for less than five drusens indicative of normal age progression.

Embodiment 4: The method of any one of Embodiments 1-3, wherein, within the dataset, AMD is defined as advanced and late stage AMD with apparent macular damage from either dry AMD or wet AMD.

Embodiment 5: The method of any one of Embodiments 1-4, wherein, within the dataset, DR is defined as moderate to proliferative DR, as classified according to the International Clinical Diabetric Retinopathy Disease Severity Scale.

Embodiment 6: The method of Embodiment 5, wherein, within the dataset, diabetic macular edema (DME) is defined as one or more of retinal thickening within 500 micrometers of a macular center, hard exudates within 500 micrometers of the macular center with adjacent retinal thickening, or one or more disc diameters of retinal thickening that are within one disc diameter of the macular center.

Embodiment 7: The method of any one of Embodiments 1-6, wherein, within the dataset, glaucoma is defined as having one or both of concentric expansion with an optic cup-to-disc ratio greater than or equal to 0.5, or narrowing of a disc at either a superior or inferior rim with a localized nerve fiber layer defect.

Embodiment 8: The method of any one of Embodiments 1-7, wherein, within the dataset, glaucoma is defined as having two or more of a vertical optic cup-to-disc ratio greater than or equal to 0.8, superior or inferior disc notch or rim thinning, or a retinal nerve fiber layer (RNFL) defect radiating from an optic nerve head.

Embodiment 9: The method of any one of Embodiments 1-8, wherein, within the dataset, RVO is defined as non-ischemic and ischemic central RVO and major and macular branch RVO.

Embodiment 10: The method of any one of Embodiments 1-9, wherein the machine-learning classifier comprises a convolutional neural network.

Embodiment 11: The method of Embodiment 10, wherein the method further comprises using the at least one hardware processor to train the machine-learning classifier by: initially training the convolutional neural network to discriminate between objects using a non-domain dataset that contains no ophthalmic images labeled with the one or more disorders; subsequently retraining one or more final layers in the convolutional neural network using the domain dataset.

Embodiment 12: The method of Embodiment 11, wherein a number of images in the non-domain dataset is at least six times greater than a number of images in the domain dataset.

Embodiment 13: The method of any one of Embodiments 1-12, wherein the ophthalmic image data comprises an image of an internal structure of a human eye.

Embodiment 14: The method of any one of Embodiments 1-13, further comprising using the at least one hardware processor to, when the at least one classification is one of the one or more disorder classifications, use regression analysis to determine a severity of a disorder associated with the one disorder classification, wherein the report further indicates the determined severity of the disorder.

Embodiment 15: The method of any one of Embodiments 1-14, wherein, when the at least one classification is one of the one or more disorder classifications, the report comprises one or more recommendations for treatment of a disorder associated with the one disorder classification.

Embodiment 16: The method of any one of Embodiments 1-15, wherein, when the at least one classification is one of the one or more disorder classifications, the report comprises an image from the ophthalmic image data that shows areas of importance used by the machine-learning classifier.

Embodiment 17: The method of any one of Embodiments 1-16, wherein the report comprises probabilities of the plurality of classifications based on a Softmax function.

Embodiment 18: The method of any one of Embodiments 1-17, further comprising using the at least one hardware processor to, after receiving the ophthalmic image data and before applying the machine-learning classifier:
determining a type of the ophthalmic image data; and
selecting the machine-learning classifier, that is associated with the determined type of the ophthalmic image data, from a plurality of different machine-learning classifiers associated with a plurality of different types of ophthalmic image data.

Embodiment 19: The method of any one of Embodiments 1-18, wherein applying the machine-learning classifier comprises segmenting vessels in the ophthalmic image data using a U-net architecture.

Embodiment 20: The method of Embodiment 19, wherein an activation function after each convolutional layer in the U-net architecture comprises a rectifier linear unit (ReLU).

Embodiment 21: The method of any one of Embodiments 1-20, wherein the ophthalmic image data comprises video, and wherein the method further comprises using the at least one hardware processor to, before applying the machine-learning classifier, stich a plurality of frames of the video together to generate a composite image to which the machine-learning classifier is applied.

Embodiment 22: The method of any one of Embodiments 1-21, wherein the at least one hardware processor is comprised within a server system, wherein receiving ophthalmic image data comprises receiving the ophthalmic image data over at least one network from a user device, and wherein providing a report comprises sending the report over the at least one network to the user device.

Embodiment 23: The method of Embodiment 22, wherein the user device is a mobile device.

Embodiment 24: The method of any one of Embodiments 1-23, further comprising using at least one hardware processor in a mobile device to:
when a connection to a remote server is available via at least one network, transmit the ophthalmic image data to the remote server for classification by a remote version of the machine-learning classifier; and,
when no connection to the remote server is available, apply a local version of the machine-learning classifier to the ophthalmic image data.

Embodiment 25: The method of any one of Embodiments 1-24, wherein receiving ophthalmic image data comprises, at a mobile device, capturing ophthalmic image data using an ophthalmosocope that is detachably coupled to the mobile device.

Embodiment 26: The method of any one of Embodiments 1-25, further comprising using the at least one hardware processor to generate a graphical user interface for a display of the mobile device, wherein the graphical user interface comprises one or more instructions for capturing the ophthalmic image data using the ophthalmoscope.

Embodiment 27: The method of any one of Embodiments 1-26, further comprising using the at least one hardware processor to train the machine-learning classifier to exhibit a sensitivity of at least 90% and a specificity of at least 90%.

Embodiment 28: The method of any one of Embodiments 1-27, further comprising using the at least one hardware processor to train the machine-learning classifier to exhibit an area under the curve (AUC) of at least 0.9.

Embodiment 29: The method of any one of Embodiments 1-28, further comprising using the at least one hardware processor to train the machine-learning classifier using a deep-learning procedure.

Embodiment 30: The method of any one of Embodiments 1-29, wherein the ophthalmic image data comprises a retinal image.

Embodiment 31: The method of any one of Embodiments 1-30, wherein the ophthalmic image data comprises a fundus image.

Embodiment 32: The method of any one of Embodiments 1-31, wherein the one or more disorder classifications are a plurality of disorder classifications, and wherein the plurality of disorder classifications further comprise at least one of a cataract, myopia, kidney disease, hypertension, or stroke.

Embodiment 33: A system comprising: at least one hardware processor; and one or more software modules configured to, when executed by the at least one hardware processor, perform the method of any one of Embodiments 1-32.

Embodiment 34: The system of Embodiment 33, wherein the system comprises an electronic kiosk comprising the at least one hardware processor and the one or more software modules.

Embodiment 35: The system of Embodiment 33 or 34, wherein the electronic kiosk comprises: an imaging component configured to capture the ophthalmic image data; and a head positioner, wherein the head positioner comprises a chin rest and a forehead rest configured to align a human eye with the imaging component.

Embodiment 36: A non-transitory computer-readable medium having instructions stored thereon, wherein the instructions, when executed by a processor, cause the processor to perform the method of any one of Embodiments 1-32.

What is claimed is:

1. A method comprising:
 a) using at least one hardware processor to:
  receive ophthalmic image data;
  apply a machine-learning classifier, trained using a domain dataset of ophthalmic images that have been labeled with one or more of a plurality of classifications, to classify the received ophthalmic image data into at least one of the plurality of classifications, wherein the machine-learning classifier comprises a convolutional neural network, wherein the plurality of classifications comprise a normal classification and one or more disorder classifications, wherein the one or more disorder classifications comprise at least one of age-related macular degeneration (AMD), diabetic retinopathy (DR), glaucoma, or retinal vein occlusion (RVO); and
  provide a report that indicates the at least one classification of the received ophthalmic image data; and
 b) using the at least one hardware processor to train the machine-learning classifier by:
  initially training the convolutional neural network to discriminate between objects using a non-domain dataset that contains no ophthalmic images labeled with the one or more disorders; and
  subsequently retraining one or more final layers in the convolutional neural network using the domain dataset.

2. The method of claim 1, wherein, within the dataset, the normal classification is defined as: (a) optic discs presenting with sharp margins and a cup-to-disc ratio within a predetermined range, striated sheen from a healthy retinal nerve fiber layer, no lesions, no apparent sub-retinal disruptions, no pigmentary changes, no tumors, no scars, no molds, and normal vasculature, with an exception for drusens indicative of normal age progression; or (b) no clinically abnormal features, no known ocular disease, and hemoglobin A1C levels less than 6.0%, with an exception for less than five drusens indicative of normal age progression.

3. The method of claim 1, wherein, within the dataset, AMD is defined as advanced and late stage AMD with apparent macular damage from either dry AMD or wet AMD.

4. The method of claim 1, wherein, within the dataset, DR is defined as moderate to proliferative DR, as classified according to International Clinical Diabetic Retinopathy Disease Severity Scale.

5. The method of claim 4, wherein, within the dataset, diabetic macular edema (DME) is defined as one or more of retinal thickening within 500 micrometers of a macular center, hard exudates within 500 micrometers of the macular center with adjacent retinal thickening, or one or more disc diameters of retinal thickening that are within one disc diameter of the macular center.

6. The method of claim 1, wherein, within the dataset, glaucoma is defined as having one or both of concentric expansion with an optic cup-to-disc ratio greater than or equal to 0.5, or narrowing of a disc at either a superior or inferior rim with a localized nerve fiber layer defect.

7. The method of claim 1, wherein, within the dataset, glaucoma is defined as having two or more of a vertical optic cup-to-disc ratio greater than or equal to 0.8, superior or inferior disc notch or rim thinning, or a retinal nerve fiber layer (RNFL) defect radiating from an optic nerve head.

8. The method of claim 1, wherein, within the dataset, RVO is defined as non-ischemic and ischemic central RVO and major and macular branch RVO.

9. The method of claim 1, wherein the ophthalmic image data comprises an image of an internal structure of a human eye.

10. The method of claim 1, further comprising using the at least one hardware processor to, when the at least one classification is one of the one or more disorder classifications, use regression analysis to determine a severity of a disorder associated with the one disorder classification, wherein the report further indicates the determined severity of the disorder.

11. The method of claim 1, wherein, when the at least one classification is one of the one or more disorder classifications, the report comprises: (a) one or more recommendations for treatment of a disorder associated with the one disorder classification; or (b) an image from the ophthalmic image data that shows areas of importance used by the machine-learning classifier.

12. The method of claim 1, further comprising using the at least one hardware processor to, after receiving the ophthalmic image data and before applying the machine-learning classifier:
 determining a type of the ophthalmic image data; and
 selecting the machine-learning classifier, that is associated with the determined type of the ophthalmic image data, from a plurality of different machine-learning classifiers associated with a plurality of different types of ophthalmic image data.

13. The method of claim 1, wherein applying the machine-learning classifier comprises segmenting vessels in the ophthalmic image data using a U-net architecture.

14. The method of claim 13, wherein an activation function after each convolutional layer in the U-net architecture comprises a rectifier linear unit (ReLU).

15. The method of claim 1, wherein the ophthalmic image data comprises video, and wherein the method further comprises using the at least one hardware processor to, before applying the machine-learning classifier, stich a plurality of frames of the video together to generate a composite image to which the machine-learning classifier is applied.

16. The method of claim 1, wherein receiving ophthalmic image data comprises, at a mobile device, capturing ophthalmic image data using an ophthalmoscope that is detachably coupled to the mobile device.

17. The method of claim 1, wherein the ophthalmic image data comprises a retinal image or a fundus image.

18. The method of claim 1, wherein the one or more disorder classifications are a plurality of disorder classifications, and wherein the plurality of disorder classifications further comprise at least one of a cataract, myopia, kidney disease, hypertension, or stroke.

* * * * *